(12) United States Patent
Liu et al.

(10) Patent No.: US 10,690,653 B2
(45) Date of Patent: Jun. 23, 2020

(54) FLUID SEPARATOR FOR POINT OF CARE MOLECULAR DIAGNOSTICS

(71) Applicant: The Trustees of The University of Pennsylvania, Philadelphia, PA (US)

(72) Inventors: Changchun Liu, Bala Cynwyd, PA (US); Haim H. Bau, Swarthmore, PA (US); Michael G. Mauk, Greelville, DE (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/534,810

(22) PCT Filed: Nov. 9, 2015

(86) PCT No.: PCT/US2015/059679
§ 371 (c)(1),
(2) Date: Jun. 9, 2017

(87) PCT Pub. No.: WO2016/093999
PCT Pub. Date: Jun. 16, 2016

(65) Prior Publication Data
US 2017/0343533 A1    Nov. 30, 2017

Related U.S. Application Data

(60) Provisional application No. 62/091,085, filed on Dec. 12, 2014.

(51) Int. Cl.
*G01N 33/49* (2006.01)
*G01N 33/00* (2006.01)
(Continued)

(52) U.S. Cl.
CPC ......... *G01N 33/491* (2013.01); *B01D 63/088* (2013.01); *B01D 2313/025* (2013.01);
(Continued)

(58) Field of Classification Search
CPC ................. G01N 33/00; G01N 33/491; G01N 2001/4088; B01D 63/088; B01D 2313/14;
(Continued)

(56) References Cited

U.S. PATENT DOCUMENTS 4,963,325 A    10/1990   Lennon et al.
5,169,789 A  * 12/1992   Bernstein ........... G01N 33/5302
                                                        422/413
(Continued)

FOREIGN PATENT DOCUMENTS

AU    2009218752 B2    7/2014
EP       0336483 A1   10/1989
(Continued)

OTHER PUBLICATIONS

Liu et al., Membrane-based sedimentation-assisted plasma separator for point-of-care applications. Oct. 5, 2013. Analytical Chemistry, vol. 85; abstract; figures 1, 3; pp. 10463, 10465-10467.
(Continued)

*Primary Examiner* — John Kim
(74) *Attorney, Agent, or Firm* — BakerHostetler

(57) ABSTRACT

The present disclosure provides devices and methods using separating a fluid—e.g., plasma or serum—from whole blood. In some embodiments, the devices and methods use hydrophobic or superhydrophobic surfaces to encourage whole blood to contact a selective membrane that extracts the desired fluid component from the blood.

20 Claims, 20 Drawing Sheets

(51) Int. Cl.
  *B01D 63/08* (2006.01)
  *B01L 3/00* (2006.01)
  *G01N 1/40* (2006.01)

(52) U.S. Cl.
  CPC ..... *B01D 2313/14* (2013.01); *B01L 3/502753* (2013.01); *B01L 2200/025* (2013.01); *B01L 2200/0605* (2013.01); *B01L 2300/0681* (2013.01); *B01L 2300/0816* (2013.01); *B01L 2300/161* (2013.01); *B01L 2300/165* (2013.01); *B01L 2400/0406* (2013.01); *B01L 2400/0463* (2013.01); *G01N 33/00* (2013.01); *G01N 2001/4088* (2013.01)

(58) Field of Classification Search
  CPC ......... B01D 2313/025; B01L 2300/165; B01L 2300/0681; B01L 2300/0816; B01L 2300/161; B01L 2200/0605; B01L 2200/025; B01L 3/502753; B01L 2400/0406; B01L 2400/0463
  See application file for complete search history.

(56) References Cited

U.S. PATENT DOCUMENTS

| | | | |
|---|---|---|---|
| 5,254,248 A | 10/1993 | Nakamura | |
| 6,106,732 A | 8/2000 | Johnston et al. | |
| 8,691,592 B2 | 4/2014 | Chen et al. | |
| 8,697,007 B2 | 4/2014 | Bau et al. | |
| 8,911,938 B2 | 12/2014 | Mauk et al. | |
| 9,233,368 B2 | 1/2016 | Bau et al. | |
| 2008/0280285 A1 | 11/2008 | Chen et al. | |
| 2010/0112723 A1 | 5/2010 | Battrell et al. | |
| 2012/0024788 A1 | 2/2012 | Kelso et al. | |
| 2012/0245042 A1 | 9/2012 | Liu et al. | |
| 2013/0112612 A1 | 5/2013 | Blankenstein et al. | |
| 2013/0164779 A1 | 6/2013 | Kelley et al. | |
| 2013/0209331 A1 | 8/2013 | Rodenfels et al. | |

FOREIGN PATENT DOCUMENTS

| | | |
|---|---|---|
| EP | 2413138 A2 | 2/2012 |
| WO | 2006/122311 A2 | 11/2006 |
| WO | 2008/076395 A2 | 6/2008 |
| WO | 2008/130463 A2 | 10/2008 |
| WO | 2009/109997 A1 | 9/2009 |
| WO | 2013/103360 A1 | 7/2013 |

OTHER PUBLICATIONS

Balu et al., "Patterning of superhydrophobic paper to control the mobility of micro-liter drops from two-dimensional lab-on-paper applications", Lab on a Chip, Jan. 1, 2009, vol. 9, No. 21, p. 3066.

* cited by examiner

Cross section of closed plasma separator

Various shapes

FLUID SEPARATOR FOR POINT OF CARE MOLECULAR DIAGNOSTICS

CROSS-REFERENCE TO RELATED APPLICATIONS

This application is the National Stage Application of International Patent Application No. PCT/US2015/059679, filed Nov. 9, 2015, which claims priority to U.S. Application No. 62/091,085, "Superhydrophobic Plasma Separator For Point of Care Molecular Diagnostics" (filed Dec. 12, 2014), which applications are incorporated herein by reference in their entireties for any and all purposes.

GOVERNMENT RIGHTS

This invention was made with government support under grants K25AI099160, R21AI112713, and R41AI104418, awarded by the National Institutes of Health. The government has certain rights in the invention.

TECHNICAL FIELD

The present disclosure relates to the field of blood-plasma separation and to the field of microfluidic devices.

BACKGROUND

Many blood-based assays require the separation of plasma or serum from whole blood, but this separation is often difficult and requires trained operator to perform. HIV is one example of an assay in which separation of blood or serum from whole blood is needed.

With specific regard to HIV, over two-thirds of the estimated 34 million people living with HIV/AIDS worldwide reside in developing countries, and nearly three-fourths of the 2.5 million new HIV infections in 2011 occurred in these countries. HIV viral load testing is critical for monitoring antiretroviral treatment (ART), allowing for an early detection of ART failure.

Plasma specimens are considered the most reliable medium for HIV viral load monitoring. Although centrifuges are ubiquitous in clinical laboratories to extract plasma from whole blood, centrifugation is not appropriate for point of care (POC) testing and is often unavailable in resource-constrained settings due to lack of laboratory infrastructure. Suitable alternatives are not readily available to separate a large volume of plasma from undiluted blood. Accordingly, there is a need in the art for improved POC devices for plasma and/or serum separation, especially from fingerprick or heel-prick whole blood (having a volume of, e.g., 250-500 μL).

SUMMARY

In meeting these long-felt needs, the present disclosure provides devices for biological fluid separation, comprising: an upper surface and a lower surface, the device being configured such that in an open state, the lower surface is in fluid communication with the environment exterior to the device, the device being configured such that in a closed state, the upper and lower surfaces are positioned opposite one another so as to define a volume between the surfaces, at least one separation membrane being disposed in the upper surface, the separation membrane being positioned so as to be in fluid communication with the volume between the surfaces when the device is in the second state, the separation membrane being selectively permeable to a fluid blood component.

The present disclosure also provides devices for biological fluid separation, comprising upper and lower surfaces, at least one of the upper surface and the lower surface comprising a hydrophobic region, a superhydrophobic region, or both, the upper and lower surfaces being connected by a hinge, the device being configured such that in an open state, the hydrophobic region, the superhydrophobic region, or both is in fluid communication with an environment exterior to the device, the device being configured such that in a closed state, the upper and lower surfaces are positioned opposite one another so as to define a volume between the surfaces, the volume between the surfaces further defined by a spacer positioned between the surfaces, at least one separation membrane being disposed in the upper surface, the separation membrane being positioned so as to be in fluid communication with the volume when the device is in the closed state, the separation membrane being selectively permeable to fluid; and a fluid collection channel configured to be in fluid communication with the separation membrane when the device is in the closed state.

Also provided are methods of separating plasma, serum, or both, comprising: disposing a blood sample on a first surface of a device, wherein the first surface comprises a superhydrophobic region, a hydrophobic region, or both such that the superhydrophobic region, the hydrophobic region, or both is in fluid communication with an environment exterior to the device; positioning the first surface opposite a second surface comprising a hydrophobic region, a superhydrophobic region, or both so as to define a volume between the surfaces, the positioning being performed so as to effect passage of plasma, serum, or both from the blood sample through a separation membrane being disposed in the second surface; and collecting plasma, serum, or both that has passed through the separation membrane.

Further provided are methods of separating a biological fluid, comprising: disposing an amount of blood onto at least one of first and second surfaces, positioning the first and second surfaces such that the blood is encouraged into contact with a separation membrane disposed in the second surface, the separation membrane being selectively permeable to a biological fluid; and collecting the biological fluid that passes through the separation membrane.

The present disclosure also provides methods of separating a fluid from a particulate suspension, comprising: disposing an amount of the particulate suspension onto at least one of first and second surfaces, at least one of the first surface and second surface comprising a hydrophobic region, a superhydrophobic region, or both, positioning the first and second surfaces such that the particulate suspension is encouraged into contact with a separation membrane disposed in the second surface, the separation membrane being selectively permeable to the fluid, and collecting the fluid that passes through the separation membrane.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

Figure 1:
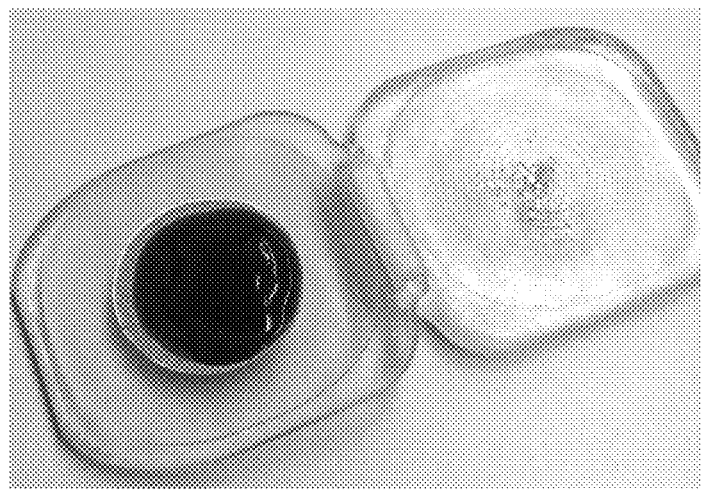
FIG. 1: an exemplary clamshell-type device according to the present disclosure.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In one aspect, the present disclosure provides devices for plasma separation, comprising upper and lower surfaces, which surfaces may be configured to oppose one another. In some embodiments, one or both surfaces comprises a hydrophobic region, a superhydrohobic region, or both. By "superhydrophobic" is meant a surface that effects a contact angle with water of at least about 150 degrees. The upper and lower surfaces may also comprise one or more hydrophobic regions. By "hydrophobic" is meant a surface that effects a contact angle with water of between at least about 90 degrees and up to about 150 degrees.

In some embodiments, the hydrophobic surface may effect a contact angle with water of between at least about 100 degrees, at least about 110 degrees, or at least about 130 degrees. By "non-hydrophobic" is meant a surface that effects a contact angle with water of less than at least about 90 degrees. Suitable such surfaces and the materials from which they are made are known to those of skill in the art and are also described herein in illustrative fashion.

The devices may be configured such that in a first state (e.g., an open state), the lower surface is in fluid communication with the environment exterior to the device. As one example, the device may be constructed with a hinged, clamshell configuration wherein the first state is an "open" state in which the lower surface is exposed to the environment exterior to the device and can receive a sample (e.g., blood) that is dripped, pipetted, or otherwise disposed on the surface.

Figure 2:
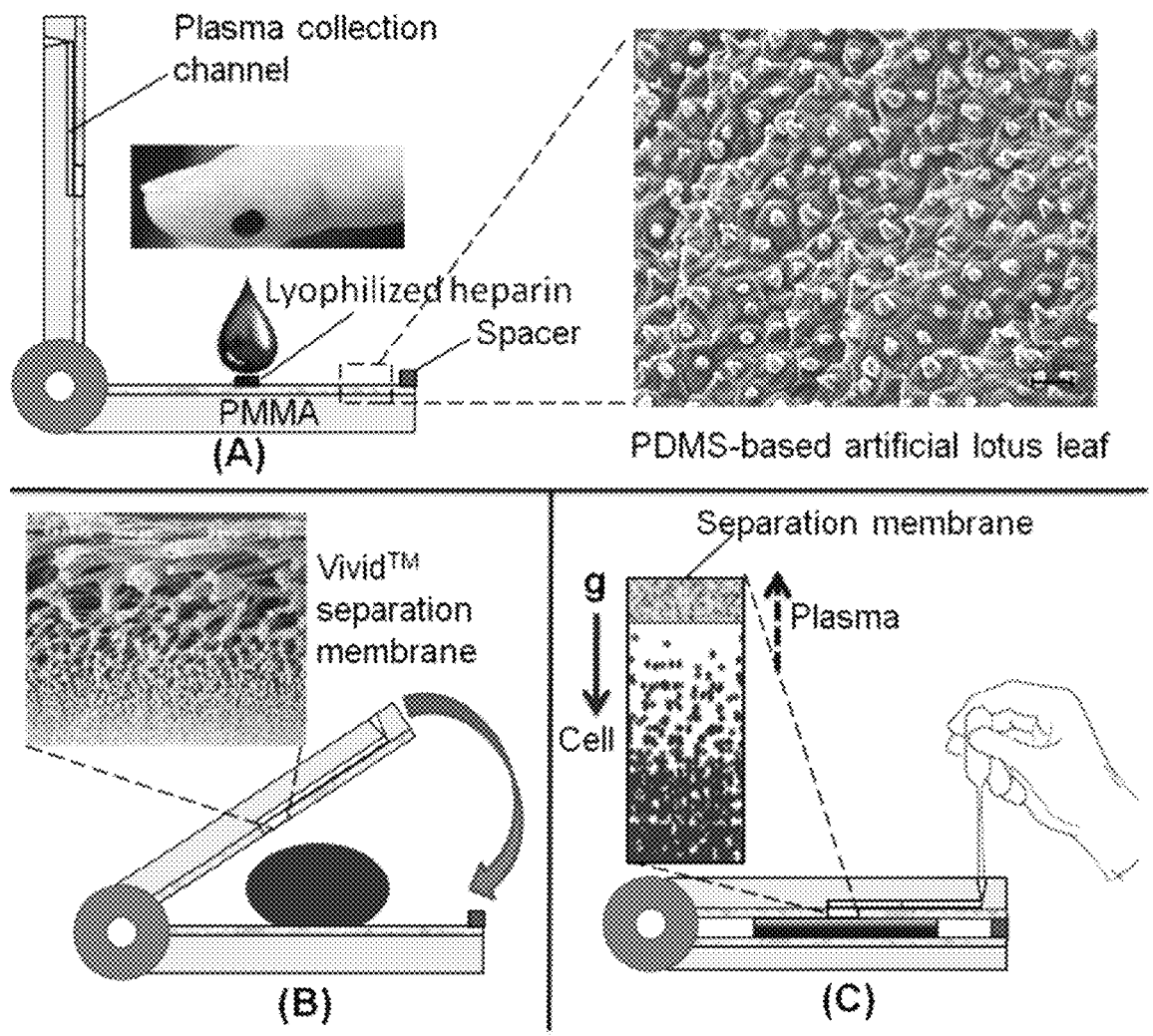
FIGS. 2A-2C: The working principle and operation of an exemplary superhydrophobic plasma separator. (A) Finger-prick blood is dropped on the bottom superhydrophobic substrate containing lyophilized heparin. Inset is SEM image of PDMS artificial lotus leaf fabricated by PI [10]. (B) When the top superhydrophobic cover with separation membrane is closed down, blood is sandwiched between the two superhydrophobic surfaces and forms a thin film. Inset is SEM image of Vivid™ separation membrane. (C) After the sandwiched blood film has been left to sediment gravitationally for a few minutes, the top blood layer is much clearer than the bottom layer as shown in the greatly enlarged inset. The solid arrow and dashed arrow illustrate, respectively, the direction of cell sedimentation and plasma flow. The plasma may be collected by a disposable pipette, or enter a downstream nucleic acid-capturing membrane (i.e., Whatman™ FTA™ membrane) embedded in a microfluidic chip. It should be understood that the presently disclosed technology is applicable to plasma separation, serum separation, or both.

The devices are also suitably configured such that in a second state, the upper and lower surfaces are positioned opposite one another so as to define a volume between the surfaces. This is shown in FIG. 2, which figure shows the device in a "closed" configuration in which the upper and lower surfaces contact the blood disposed therebetween. As described elsewhere herein, the device need not be a clamshell or hinged configuration, as devices may also have two surface that are separate from one another and are then positioned (e.g., by tabs, screw-down, or click-in mechanisms) by the user at the appropriate time.

A device may include at least one separation membrane disposed in the upper surface. This membrane is suitably positioned so as to be in fluid communication with the volume defined between the surfaces when the device is in the second state, and the separation membrane being selectively permeable to fluid. Suitable such membranes are described elsewhere herein; membranes that are permeable to plasma, serum, or even both are considered especially suitable, e.g., a membrane that is permeable to plasma but not to whole blood. Devices and methods according to the present disclosure may also be configured to effect serum separation, e.g., via (through the presence of a reagent) precipitation or other separation of clotting factors/fibrinogens present in plasma.

The devices may be configured such that in the second or closed configuration, an enclosed volume (e.g., a cube-shaped volume, a puck-shaped volume, or any other volume shape) is defined between the supper and lower surfaces. The volume may be in fluid isolation from the environment exterior to the volume. The only fluid communication between the volume and the exterior environment may be via the permeable membrane, described elsewhere herein.

A device may include a fluid collection channel configured to be in fluid communication with the separation membrane when the device is in the second state. This is shown in FIG. 2(C), which figure shows a user collecting plasma (or serum, not shown) from a collection channel after the fluid has passed through the separation membrane.

In some embodiments, the volume between the surfaces is further defined by a spacer. Such a spacer is shown in FIG. 2(A). A spacer is not necessary, as a device may be constructed (e.g., FIG. 10) such the device has a well bounded by a lower surface and the well is then sealed by an upper surface when the device is in a second state; no spacer is necessary.

In some embodiments, the device may include one or more reagents disposed within (e.g., within the volume between the two surfaces) or even on the device. Such reagents may be disposed on one or both of the upper or lower surfaces, and may even be disposed on a hydrophobic or superhydrophobic region of a surface or even on a hydrophilic region of the device or even on the separation membrane.

Suitable reagents include reagents that affect clotting or other blood properties (e.g., lyophilized heparin, citrate, coagulants, EDTA, lyophilized heparin, and the like). Other suitable reagents include antibodies, antigens, dyes, oligo-nucleotides (e.g., primers), and the like. Such reagents may be used to participate in a downstream process (e.g., PCR, antibody detection, and the like).

A lower surface suitably includes a hydrophobic, superhydrophobic or hydrophobic and superhydrophobic region, but may also include a hydrophilic region. The hydrophilic region may act as a base or landing location for blood disposed into the well. In this way, blood is localized at the by hydrophilic spot (by the action of the superhydrophobic surfaces) and is then contacted with the plasma (or serum) separation membrane. The hydrophilic region of the lower surface may be at least partially in register with the membrane when the device is in the second (e.g., closed) state, though this is not a requirement.

The separation membrane may be selectively permeable to blood plasma or even selectively permeable to blood serum. In some embodiments, the separation membrane is hydrophilic. In some embodiments, the separation membrane is superhydrophobic.

Figure 10:
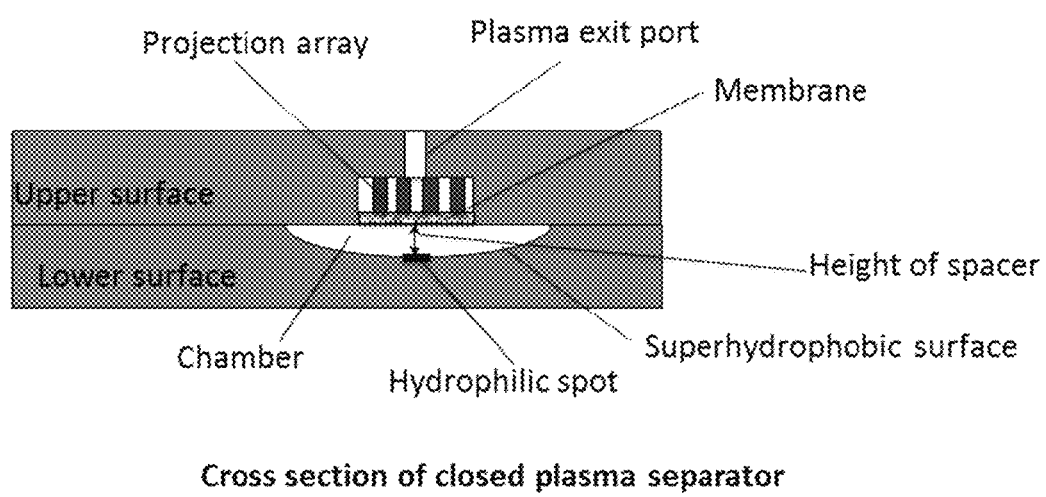
FIG. 10: Illustrates an embodiment of a cross section of an exemplary plasma separator, as well as the various shapes the one or more projections configured to support the separation membrane can assume.
Figure 10:
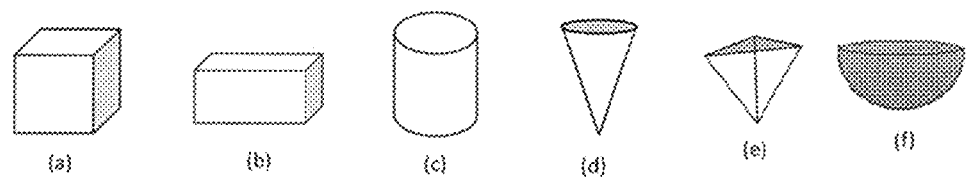

A device may further comprise one or more projections configured to support the separation membrane. This is shown in FIG. 10, which figure shows a cross section of the device comprising a projection array positioned above the membrane. In some embodiments, one or more of the projections comprises a micropillar, microcone or a microhexahedron. This is shown in FIG. 10, which figure illustrates examples of such shapes.

The upper and lower surfaces are positioned opposite one another such that the distance between the surfaces is between about 1 µm and about 1 cm. In some embodiments, the distance between the surfaces is between about 1 µm and about 10 mm, or between about 10 µm and about 5 mm, or even about 1 mm. It should be understood that the distance between the surfaces need not be constant, as the surfaces need not be flat and need not be parallel to one another. As one example, one surface may be flat, and the other surface may slope towards or away from the first surface. A surface may be convex, concave, pitted, or otherwise non-planar.

The volume between the surfaces may be in the range of from about 1 µL and about 5,000 µL. In some embodiments, the volume between the surfaces is between about 10 µL and about 300 µL. In some embodiments, the volume between the surfaces is between about 10 µL and about 100 µL. In some embodiments, the volume is about 10 µL, 20 µL, 30

μL, 40 μL, 50 μL, 60 ηL, 70 μt, 80 μL, 90 μL, 100 μL, 200 μL, 300 μL, 400 μL, 500 μL, 600 μL, 700 μL, 800 μL, 900 μL or even about 1,000 μL.

It should be understood that the region between the surfaces (e.g., the volume) need not be entirely enclosed, although it may be enclosed. As shown in FIG. 2, the hydrophobic/superhydrophobic nature of the surfaces acts to encourage the fluid into a particular position, and it is not in all cases necessary for the fluid to be completely physically enclosed.

In some embodiments, the upper and lower surfaces may be connected by a hinge. The hinge provides for a clamshell configuration of the device, wherein the first state is an "open" state in which the lower surface is exposed to the environment exterior to the device. The hinge also provides for a second state, in which the device is in a "closed" configuration in which the upper and lower surfaces contact the blood disposed therebetween. Examples of "open" and "closed" configurations are shown in FIG. 2.

Figure 11:
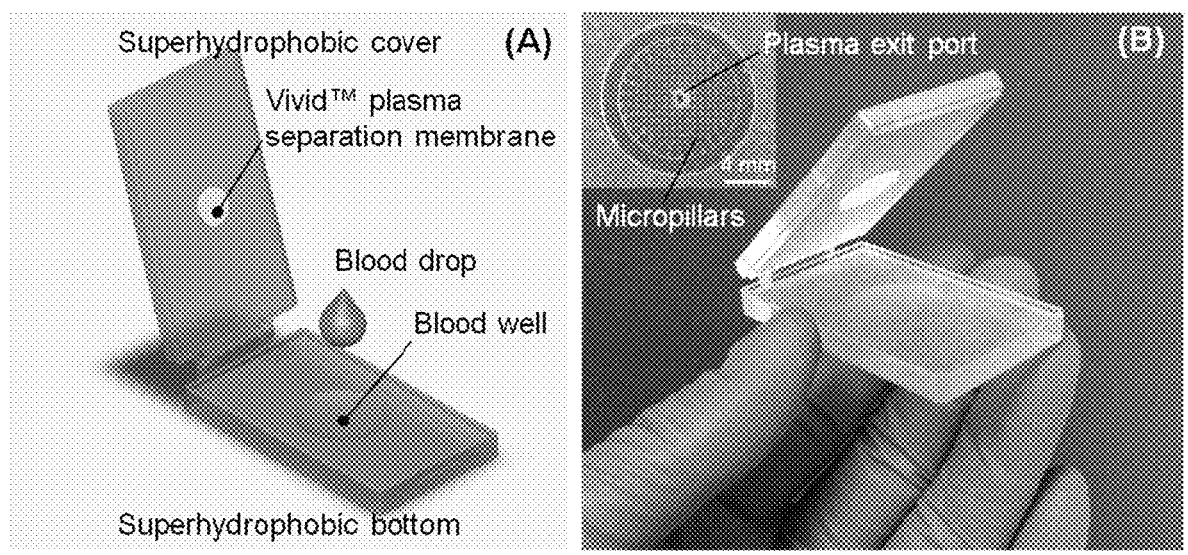
FIGS. 11A-11B: (A) A schematic illustration of a clamshell-style, superhydrophobic plasma separator. The device consists of a superhydrophobic, cover substrate with a separation membrane and a superhydrophobic bottom substrate with a blood well. (B) A photograph of the superhydrophobic plasma separator. Inset is an optical image of a micropillar array on the superhydrophobic top cover.

The device may further comprise at least one fluid exit port in fluid communication with the separation membrane. This is shown in FIG. 11, which figure shows a cross section of the device comprising an exit port situated above the membrane. Such an exit port is not limited to the configuration shown in FIG. 10.

FIG. 10 shows an exemplary embodiment of the disclosed devices, providing a cross section of a closed plasma/serum separator. As shown in the figure, a device may include upper and lower superhydrophobic surfaces, with a chamber or well for receiving a sample. The membrane is positioned above the chamber or well. The lower surface shown in the figure includes a hydrophilic region (or "hydrophilic spot," as designated in FIG. 10). The hydrophilic region may act as a base or landing location for blood disposed into the well. In this way, blood is localized at the hydrophilic spot (by the action of the superhydrophobic surfaces) and is then contacted with the plasma (or serum) separation membrane.

A projection array may be positioned above the membrane. Such projection array may comprise a micropillar, microcone or a microhexahedron, including the various shapes that are shown in FIG. 10 directly below the cross section of a closed separator. A fluid (plasma, serum) exit port, shown positioned above the projection array, may also be included. It should be understood that the array of projections is not necessary. In some embodiments, the exit port is sized such that the array of projections is not needed because the port is sufficiently small compared to the membrane. In other embodiments (not shown), there is more than one port in fluid communication with the membrane. In some such embodiments, no projection array is necessary.

In another aspect, the present disclosure provides devices for biological fluid (e.g., plasma, serum) separation, comprising: upper and lower surfaces, at least one of the upper surface and the lower surface comprising a hydrophobic region, a superhydrophobic region, or both; the terms "hydrophobic" and "superhydrophobic" are defined elsewhere herein.

A device may be configured such that the upper and lower surfaces are connected by a hinge. The hinge provides for a clamshell configuration of the device, wherein the first state is an "open" state in which the lower surface is exposed to the environment exterior to the device. The hinge also provides for a second state, in which the device is in a "closed" configuration in which the upper and lower surfaces contact the blood disposed therebetween. Examples of "open" and "closed" configurations are shown in FIG. 2.

In this aspect, the devices may be configured such that in an "open" state, a hydrophobic region, the superhydrophobic region, or both of a surface is/are in fluid communication with the environment exterior to the device. The device may be constructed in a hinged, clamshell configuration wherein the first state is an "open" state in which the lower surface is exposed to the environment exterior to the device and can receive a sample (e.g., blood) that is dripped, pipetted, or otherwise disposed on the surface. A surface (upper or lower) may include a depression, pit, trench, carve-out, or other recess, which feature may receive the sample.

In this aspect, the devices are also suitably configured such that in a "closed" state, the upper and lower surfaces are positioned opposite one another so as to define a volume between the surfaces. This is shown in FIG. 2, which figure shows the device in a "closed" state or configuration in which the upper and lower surfaces contact the blood disposed therebetween.

In this aspect, the device also comprises a spacer to define the volume between the surfaces. An example of such a spacer is shown in FIG. 2(A). Such a spacer is not limited to the configuration shown in FIG. 2(A).

In this aspect, the device may include at least one separation membrane disposed in the upper surface. This membrane is suitably positioned so as to be in fluid communication with the volume between the surfaces when the device is in the second state, and the separation membrane being selectively permeable to fluid. Suitable such membranes are described elsewhere herein. In some embodiments, the separation membrane is selectively permeable to a blood fluid, e.g., plasma, or serum. In some embodiments, the separation membrane is hydrophilic. In some embodiments, the separation membrane is superhydrophobic.

In this aspect, a fluid collection channel may be configured to be in fluid communication with the separation membrane when the device is in the second state. This is shown in FIG. 2(C), which figure shows a user collecting plasma from a collection channel after the fluid (which may also be serum) has passed through the separation membrane.

In another aspect, the present disclosure provides methods of separating plasma (or serum) comprising: disposing a blood sample on a first surface comprising a superhydrophobic region and hydrophilic region such that the superhydrophobic region is in fluid communication with the environment exterior to the device; positioning the first surface opposite a second surface comprising a hydrophobic region, a superhydrophobic region, or both so as to define a volume between the surfaces, the positioning being performed to as to effect passage of plasma or serum (or both) from the blood sample through a separation membrane being disposed in the second surface; and collecting the fluid (plasma, serum) that has passed through the separation membrane.

The disposing may be direct or indirect. For example, a blood sample may be directly disposed on a first surface by direct contact from a finger-prick or with a disposable pipette. These are shown in FIG. 2. A blood sample may also be indirectly disposed by dropping the sample onto a first surface without directly contacting the surface. The disposing may also be manual or automated. The positioning may be performed as shown in FIG. 2, which figure shows the device in a "closed" configuration in which the upper and lower surfaces contact the blood disposed therebetween. As described elsewhere herein, the device need not be a clamshell or hinged configuration, as devices may also have two surface that are separate from one another and are then positioned (e.g., by tabs, screw-down, or click-in mechanisms) by the user at the appropriate time. The collecting may be performed manually, as with a disposable pipette, which is shown in FIG. 2. The collecting may also be automated.

In some embodiments, the fluid (plasma, serum) collection may be carried out by applying a negative pressure. Fluid collection may also be carried out by capillary suction.

In some embodiments, the first surface is a lower surface and the second surface is an upper surface.

In another aspect, the present disclosure provides methods of separating a biological fluid, comprising: disposing an amount of blood onto at least one of first and second surfaces. In some embodiments, at least one of the first surface and second surface comprises a hydrophobic region, a superhydrophobic region, or both. The user may position the first and second surfaces such that the blood is encouraged (e.g., by a hydrophobic or superhydrophobic region) into contact with a separation membrane disposed in the second surface, the separation membrane being selectively permeable to a blood fluid (e.g., plasma, serum), and collecting the fluid that passes through the separation membrane.

The disposing may be direct or indirect; disposition is described elsewhere herein.

The design of the first and second surfaces, e.g., one or more of the upper surface and the lower surface comprising a hydrophobic region, a superhydrophobic region, or both, may encourage the blood into contact with a separation membrane disposed in the second surface. A lower surface may also include a hydrophilic region that may act as a base or landing location for blood disposed into the well; the hydrophilic region may be in register or placed into register with the membrane. In this way, blood may be localized at the hydrophilic spot (by the action of the hydrophobic surface(s), superhydrophobic surface(s) or both) and is then contacted with the separation membrane. In this way, blood may be encouraged into contact with a separation membrane disposed in the second surface. The collecting may be performed manually, as with a disposable pipette, which is shown in FIG. 2. The collecting may also be automated.

In some embodiments, the first surface includes a hydrophilic region. The hydrophilic region may include hydrophilic material (e.g., as a film or as a coating), such as cellulose and the like. In another aspect, the present disclosure provides methods of separating a fluid of a particulate suspension, comprising: disposing an amount of the particulate suspension onto at least one of first and second surfaces, each of the first surface and second surface comprising a hydrophobic region, a superhydrophobic region, or both, positioning the first and second surfaces such that the particulate suspension is encouraged into contact with a separation membrane disposed in the second surface, the separation membrane being selectively permeable to the fluid, and collecting the fluid that passes through the separation membrane.

The present disclosure also provides methods of method of separating a fluid of a particulate suspension. Blood is one such suspension, but other fluids (e.g., biofluids, water samples, and the like) are also suitable.

The methods include disposing an amount of the particulate suspension onto at least one of first and second surfaces. Suitable disposal methods are described elsewhere herein and are known to those of ordinary skill in the art.

Each of the first surface and second surfaces suitably includes a hydrophobic region, a superhydrophobic region, or both. Suitable such surfaces are described elsewhere herein.

A user may then position the first and second surfaces such that the particulate suspension is encouraged into contact with a separation membrane disposed in the second surface. A hinge, manual movement, a screw-down, or other methods are all suitable for positioning. The the separation membrane is suitably selectively permeable to the fluid, and the user may then collect fluid that passes through the separation membrane. In this way, a user may separate the fluid of the suspension from the particulate of the suspension. The user may collect the particulates (e.g., red blood cells, bacteria, and the like), collect the fluid, or both. In some embodiments, the methods include encouraging the particulate suspension into contact with a hydrophilic region that is at least partially in register with the separation membrane.

Additional Disclosure

Natural lotus leaves are known for their "lotus effect," which makes water droplets roll off the leaf and carry away dirt particles and debris. Without being bound to any particular theory, proposed here is using the "lotus effect" so as to reduce bioparticle (HIV virus, proteins etc.) adhesion and blood cell hemolysis. One may employ a simple, rapid and low-cost method to fabricate superhydrophobic, Polydimethylsiloxane (PDMS)-based, artificial lotus leaf substrates by using a natural, fresh, lotus leaf as a template in soft lithography technology. (It should be understood that a lotus leaf is not the exclusive template for the surfaces of the disclosed devices.)

Separation membranes of current membrane-based separators may be horizontally positioned beneath the volume of whole blood. Provided here is a top-positioned membrane-based, sedimentation-assisted, separation mechanism for high-efficiency separation. The device may be, e.g., rapidly made from polymer sheets cut by a $CO_2$ laser with a total material cost of <$0.20 USD/device. Anticoagulant may be lyophilized and pre-stored in the separator. The blood will be sandwiched between two superhydrophobic artificial lotus leaf substrates to form a thin film. The separation membrane will be positioned on the top of the blood film. The gravity sedimentation time of blood will be assessed and optimized. The disclosed separators may also be used in virus recovery.

FIG. 2 illustrates the working principle and operation of the proposed separator. Blood is sandwiched between two superhydrophobic artificial lotus leaf substrates to form a thin film, which within a few minutes will efficiently separate cells from liquid layer by gravity (inset of FIG. 2C). This process may be accelerated by the thinness of the blood film. Then, the top liquid layer will be further separated from cells by use of a separation membrane such as a Vivid™ membrane. The separated plasma (or serum) may be collected by a disposable pipette, or in some embodiments enter a nucleic acid-capturing membrane. It should be understood that the disclosed separators may be placed into fluid communication with a downstream device, e.g., a lateral flow strip or other analysis device.

A plasma separator is expected to achieve a high efficiency plasma separation, e.g., with virus recovery >90% and plasma yield >80%. Similar performance may be seen in serum separation embodiments. A separation device can also be adapted to detect cell-free nucleic acids (cfNAs), protein biomarkers, and other bloodborne pathogens, e.g., HCV.

The separator described herein can be used as a stand-alone device to extract plasma (or serum) from blood. In this mode of operation, the device is suitable for onsite testing in resource-poor regions of the world, where funds, trained personnel, and laboratory facilities are in short supply and in settings lacking electrical power.

A separator according to the present disclosure may be combined with other devices, e.g., a nucleic acids testing chip as a sample preparation module, to develop a next-generation, "whole blood sample-to-answer", POC, molecular diagnostic platform.

One difficulty in creating a separation system is the extremely high proportion of cells in blood, which makes blood very prone to cause clogging issues in microchannels and filters. To address it, this disclosure proposes a top-positioned membrane-based, sedimentation-assisted, separation mechanism for high efficiency separation.

In the present disclosure, the separation membrane of the device is horizontally positioned above a thin, sandwiched blood film (FIG. 2C). Such a top-positioned membrane arrangement prevents blood cells from accumulating on the membrane surface, clogging the membrane, and reducing its separation capacity. This arrangement enables efficient flow of fluid through the membrane without blockage by blood cells and increases the membrane's capacity to handle larger volumes of blood without excessive hemolysis. This enables a high plasma (or serum) yield (e.g., >50, 60, 70, 80, or even above 90%), which is significantly higher than that of any previously reported membrane-based separator. Such high plasma yield enables the device to extract a relatively large volume of plasma (or serum, in some embodiments) (>100 µL) from 250-500 µL of finger or heel-prick blood instead of several milliliters of venipuncture blood.

As described elsewhere herein, devices may be made of low-cost plastic and can be rapidly made with a total material cost of, e.g., ~0.20 USD/device. It can work with undiluted finger or heel-prick blood and does not require well-trained personnel, electricity or a central lab site, which all are unavailable in resource-constrained settings. Furthermore, a low negative pressure provided by pipette will be sufficient to collect the plasma without a need for an external pressure pump, which makes it compatible with downstream nucleic acids test chips.

Fabrication

Figure 3:
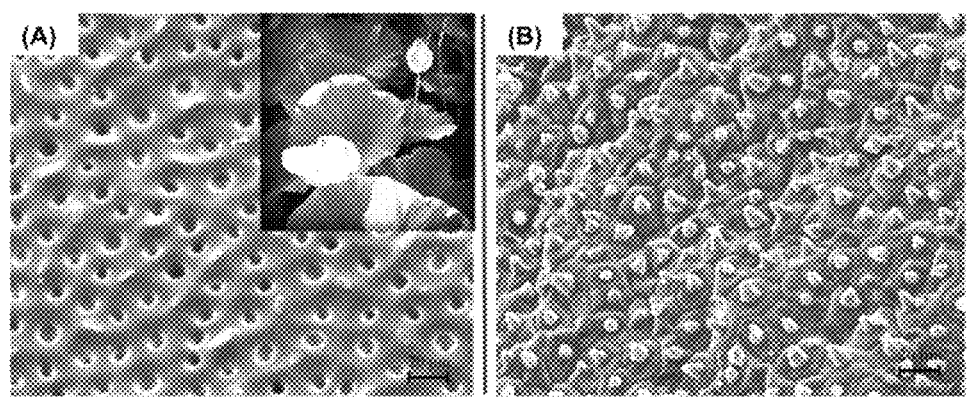
FIGS. 3A-3B: SEM images of surface morphology of PDMS negative template (A) and PDMS artificial lotus leaf (B) fabricated. Inset is a photograph of natural lotus leaves used as a template.

To obtain a superhydrophobic, artificial lotus leaf, a piece of fresh lotus leaf (inset of FIG. 3A) may directly be used as a template to cast polydimethylsiloxane (PDMS). First, PDMS prepolymer is prepared by mixing the elastomer base (Part A) and curing agent (Part B) (Sylgard® 184 Silicone) in a 10:1 ratio by weight. Next, the PDMS prepolymer is poured on the surface of a piece of clean, fresh lotus leaf (original template), and then covered with a glass plate to provide a rigid support. After solidification at room temperature for 24 h, the glass plate/PDMS layer (negative template) (FIG. 3A) is peeled off, resulting in a complementary topographic surface structure of the fresh lotus leaf. To replicate PDMS artificial lotus leaf, a second replication may be performed against the PDMS negative template (FIG. 3A) in the same manner as described above. To facilitate template release, the surface of PDMS negative template may be treated with chlorinated silanes (i.e., dimethyloctadecylchlorosilane) before casting. In this way, the complex surface patterns of the natural lotus leaf will be transferred onto the surface of PDMS artificial lotus leaf (FIG. 3B). The negative template (FIG. 3A) is reusable.

Characterization

Figure 4:
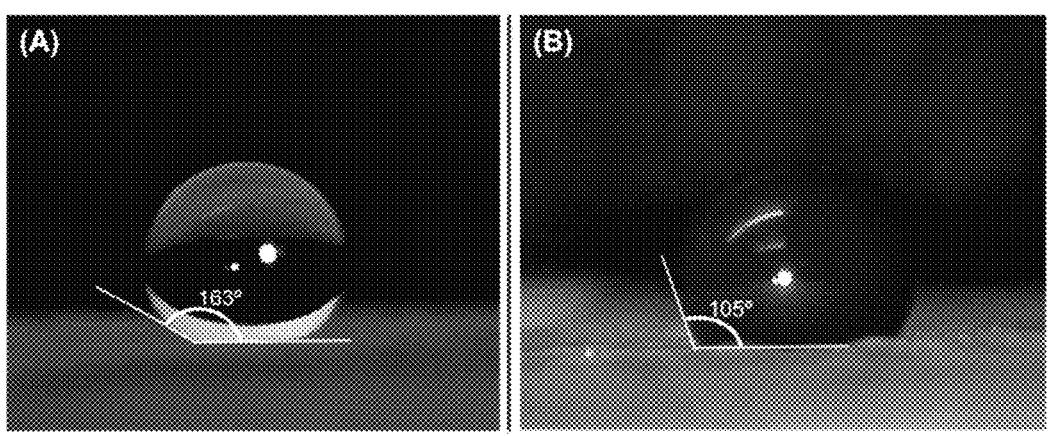
FIGS. 4A-4B: Preliminary data on photographs of a 5-µL water droplet (A) and a 5-µL blood droplet (B) on superhydrophobic PDMS artificial lotus leaf.

The morphologies of PDMS artificial lotus leaf, sputter-coated with gold, may be imaged with a FEI Quanta 600 FEG Environmental Scanning Electron Microscopy (ESEM). The static contact angles of water and fresh whole blood on superhydrophobic surface may be measured with a 5 µL of deionized (DI) water and blood droplet by a Rame-Hart standard automated goniometer. Advancing and receding contact angles may be measured by adding and removing water and blood from the substrate, respectively. For roll-off angle measurements, the substrate may be placed on a custom-designed stage with protractor. All contact angle and roll-off angle values may be averaged over four measurements. FIGS. 4A and B show photographs of a 50 µL DI water droplet and a blood droplet on the superhydrophobic, PDMS-based, artificial lotus leaf with contact angles of 163° and 105°, respectively. In addition to the PDMS-based, artificial lotus leaf, HIV Virus Adhesion Assay De-identified whole blood samples from healthy donors are provided. The HIV virus adhesion assay experiments may be performed under static conditions on superhydrophobic surface. Briefly, a superhydrophobic PDMS artificial lotus leaf with an area of 2 cm×2 cm may be brought into contact with 1 mL of blood spiked with various virus concentrations. After 1, 3, 5, 10 and 30 min., the blood is recovered and the virus concentration detected via real time quantitative PCR. Following PCR amplification, the obtained cycle threshold ($C_t$) values can be related to the number of viral copies by means of a calibration curve. The decrease in virus concentration will allow an indirect evaluation of the number of HIV viral copies adhered onto superhydrophobic surface. A PDMS substrate with flat surface may also be tested as a reference. The virus adhesion to a given surface can be expressed in number of viral copies normalized with respect to substrate surface area (i.e., in equivalent virus/$cm^2$). The mean values and standard deviation of virus adhesion data may be evaluated by, e.g., applying one-way ANOVA statistical test with a 0.05 significance level to assess whether or not differences in virus adhesion on the surfaces are significant.

Hemolysis Assay

Hemolysis should be avoided in some applications because: (i) lysis of red blood cells leads to hemoglobin in the plasma, which is a strong inhibitor of enzymatic amplification, and (ii) lysis of white blood cell will add proviral HIV DNA, which will lead to overestimation of viral load.

To assess the hemocompatibility of superhydrophobic surface, 200 µL of whole blood may be added to the superhydrophobic substrate. After a contact time of 1, 3, 5, 10 and 30 min., 4 mL of isotonic saline is added to each sample to stop hemolysis. Positive and negative controls are produced by adding 200 µL of blood to 4 mL of distilled water and isotonic saline, respectively. To establish a reference, a PDMS substrate with flat surface may also be tested. All the test samples are centrifuged. Optical density (OD) of the supernatant are measured using a spectrophotometer. The experiments may be repeated at least three times. The hemolysis rate (HR) is defined as the ratio of the OD difference between test sample ($OD_{test}$) and negative control ($OD_{negative}$) with the OD difference of positive sample ($OD_{positive}$) and negative control ($OD_{negative}$). The percent of hemolysis is calculated using (1):

$$HR (\%)=(OD_{test}-OD_{negative})/(OD_{positive}-OD_{negative})\times 100\% \quad (1)$$

Self-assembled monolayers (SAMs) of different chemical compositions may be employed to modify the surface properties of PDMS. Additionally, a silicon negative template with periodic, micro/nano binary, structure for replicating superhydrophobic PDMS substrate may be fabricated. The surface topography of such a silicon template is adjustable and can be fabricated by combining a deep reactive ion etching (DRIE) technology with an electrochemical anodization etching technique.

Separator Design and Fabrication

As PDMS has generally a soft characteristic and is prone to deform, a "hard-soft", hybrid solution may be used to fabricate poly(methyl methacrylate) (PMMA)/PDMS, superhydrophobic substrates. PMMA is suitable because it is amenable to laser machining, milling, surface modification, injection molding, and bonding. The separator may be fabricated with computer-aided design (SolidWorks™) using a $CO_2$ laser, allowing for rapid turnaround of one hour from concept to prototype at the Penn Micro and Nano Fluidics Lab.

To improve the bonding between the soft, superhydrophobic PDMS film and the rigid PMMA substrate, a 200 nm thickness $SiO_2$ film maybe deposited on PMMA substrate as an intermediate film by the plasma-enhanced chemical vapor deposition (PECVD) technology at room temperature. Before the $SiO_2$ deposition, the PMMA substrate is cleaned using ethanol at room temperature for 15 min, and treated with oxygen plasma for 2 min. A thin-casting method is used to replicate the superhydrophobic PDMS film. Briefly, PDMS prepolymer is first poured on glass plate/PDMS negative template (FIG. 3A). Then, $SiO_2$-coated PMMA substrate is placed on the casted PDMS prepolymer. After solidification at 50° C. for at least 1 h, PMMA/PDMS superhydrophobic substrate is peeled off Top-Positioned Membrane Configuration A 5 mm diameter of asymmetric, polysulfone separation membrane (Vivid™ GR, Pall Life Sciences) is cut with a $CO_2$ laser machine (Universal Laser Systems). A double-sided adhesive tape is also cut with the laser to the same external dimensions as the separation membrane. A 4 mm diameter concentric disk is then removed from the adhesive tape center to leave a ring. The adhesive ring is then attached to the separation membrane. The resulting laminate is glued on the surface of the top superhydrophobic substrate (FIG. 2A). The fluid (e.g., plasma, serum) collection channel and fluid exit are cut in the top substrate with a $CO_2$ laser. Two PMMA/PDMS superhydrophobic substrates are then assembled together by a hinge joint to form the plasma separator (FIG. 2). Alternatively, other separation membrane, such as MircoPES® TF10 capillary membrane. Primecare™ Hydrophilic Asymmetric Membranes can also be applied.

Optimization of the Thickness of Sandwiched Blood Film

As shown in FIG. 2C, by taking advantage of superhydrophobic characteristics of superhydrophobic surfaces, the blood is sandwiched between the two superhydrophobic substrates to form a thin film. The blood cells settle rapidly due to the thinness of the blood film (inset of FIG. 2C). The thickness of blood film is determined by the height of spacer (FIG. 2C). 300 µL of blood and different height of spacers (1, 1.5, 2, 2.5 and 3 mm) maybe applied to evaluate the effect of film thickness on separation efficiency.

Figure 5:
FIGS. 5A-5B: Preliminary data on side-view image of a sandwiched, blood film with a total volume of 100 µL between two the superhydrophobic, PDMS lotus leaf substrates (A) and the two PDMS substrates with flat surface (B). Scale bar is 2 mm.
Figure 5:

FIG. 5A is a side-view image of ~100 µL of blood film sandwiched between the two superhydrophobic PDMS artificial lotus leaf substrates. As observed in FIG. 5A, a well-defined blood film (a 2.5-mm thickness, 7.0-mm diameter) with an almost vertical meniscus is formed. Due to the large contact angle with the superhydrophobic surface, the sandwiched blood will contract toward its center (shown by arrows in FIG. 5A) when plasma is drawn through the membrane. This is contrasted with the case of blood sandwiched between the two PDMS substrates with flat surface, where the blood tends to spread (FIG. 5B), resulting in a low plasma separation yield. The present invention may, e.g., produce a plasma (or serum) yield of >70% within less than 10 minutes, e.g., a plasma yield of >80% may be achieved within less than 5 minutes.

Sedimentation Time

Because blood cells are approximately 10% denser than the plasma in which they are suspended, the blood cells will sink to the bottom substrate due to gravity. Sedimentation advantageously reduces clogging issues inherent to separation membrane in the top-positioned membrane arrangement, as blood cells sediment away from the entrance of the separation membrane, enabling the free flow of plasma through the membrane and improving the separation capacity of the separation membrane (inset of FIG. 2C). To optimize the sedimentation time of blood, plasma is collected from 300 µL of sandwiched blood at sedimentation times of 0, 3, 5, 7 and 10 minutes, thus indicating the volume of the extracted plasma (µL) as a function of the sedimentation time (Ts, min).

Clinical Applications

HIV may serve as a model analyte to evaluate the performance of the device by separating two sets of blood samples: i) HIV-negative blood samples spiked with known HIV virus load standards and ii) HIV-positive patient blood samples. It should be understood, however, that the disclosed technology is not limited to HIV-related applications and can in fact be applied to any application that includes separation of a fluid component (e.g., plasma, serum) from whole blood or other biological fluid.

Exemplary Hemolysis Test of Extracted Plasma

High shear stress caused by the porous separation membrane can also damage blood cells and lead to contamination of the plasma with hemoglobin. The hemoglobin concentration may be measured in relative units, using a sample of lysed whole blood as a reference. The lysed sample is made by diluting whole blood by a factor of 40 with distilled water, which causes all the hemoglobin contained in the RBCs to be released into the solution. Therefore, hemoglobin content in the reference liquid corresponds to 2.5% hemolysis. Relative hemoglobin concentrations may be evaluated with a ND-1000 spectrophotometer. To establish a reference, the total concentration of hemoglobin in centrifuged plasma produced by benchtop centrifugation may also be tested.

Virus Recovery

De-identified blood samples maybe spiked with intact HIV-1 virus (AcroMetrix® HIV-1 High Control, Benicia, Calif.) to concentrations of $1\times10^5$, $1\times10^4$, $1\times10^3$, $1\times10^2$, and $5\times10^1$ copies/mL. A separator's recovery efficiency for HIV virus maybe evaluated by comparing its performance with that of standard laboratory centrifugation procedures. To establish a reference, blood samples containing intact HIV virus at various concentrations are centrifuged at 2200-2500 RPM for at least 15 minutes with a bench-top centrifuge at room temperature. Both extracted plasma produced by the disclosed plasma separator and centrifuged plasma produced by centrifugation are analyzed by standard quantitative PCR to determine the viral load. The recovery efficiency (RR) is defined as the ratio of the number of virus copies ($C_{device}$) in the plasma separated with the superhydrophobic plasma separator and the number of virus copies ($C_{centrifuge}$) in plasma obtained by centrifugation from the same blood sample. The recovery efficiency (RR) of HIV virus of the plasma separator may be determined as a function of the blood viral load (viral RNA copies/mL) using (2):

$$\text{RR } (\%) = C_{device}/C_{centrifuge} \times 100\% \qquad (2)$$

Figure 6B:
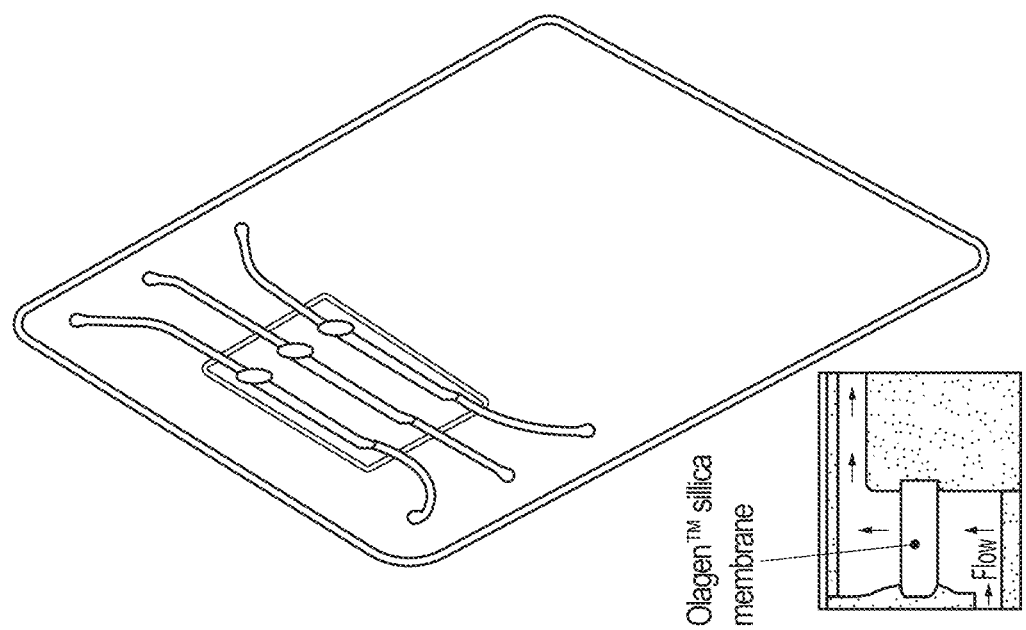
FIGS. 6A-6C: (A) Recovery efficiency of HIV virus of alternative plasma separator as a function of blood viral load. (B) Photograph of microfluidic nucleic acid testing chip. Inset: a schematic illustration of the flow-through operation for nucleic acid extraction. (C) Real-time monitoring of RT-LAMP amplification of plasma samples extracted with the plasma separator and spiked with (1) $3.5 \times 10^4$, (2) $3.5 \times 10^3$, (3) $3.5 \times 10^2$, and (4) 0 (negative control) viral RNA copies per/mL. Inset: the threshold time Tt (min) as a function of the HIV concentration (n=3) [9].
Figure 6A:
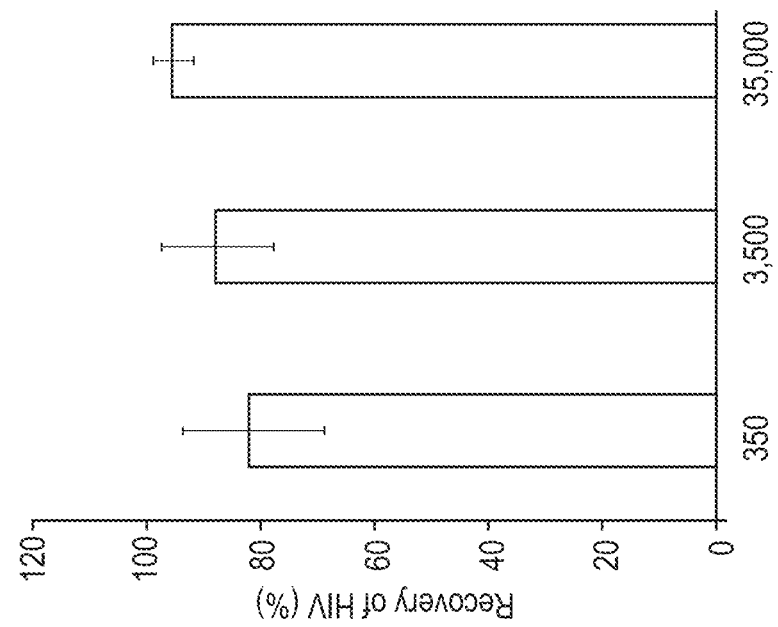

In one non-limiting experiment, the devices obtained a virus recovery of 81.5% for low viral load samples ($3.5 \times 10^2$ copies/mL), and 95.5% for high viral load samples ($3.5 \times 10^4$ copies/mL), respectively (FIG. 6A).

To determine repeatability and reproducibility, three virus concentrations ($10^5$, $10^3$, and $10^2$ copies/mL) may be tested 8 times each using separate devices to validate repeatability. To analyze reproducibility, both intra- and inter-assay coefficients of variation (CV) may be determined. CV values are calculated as the standard deviation "a" divided by the mean "μ" (CV=σ/μ).

Figure 6C:
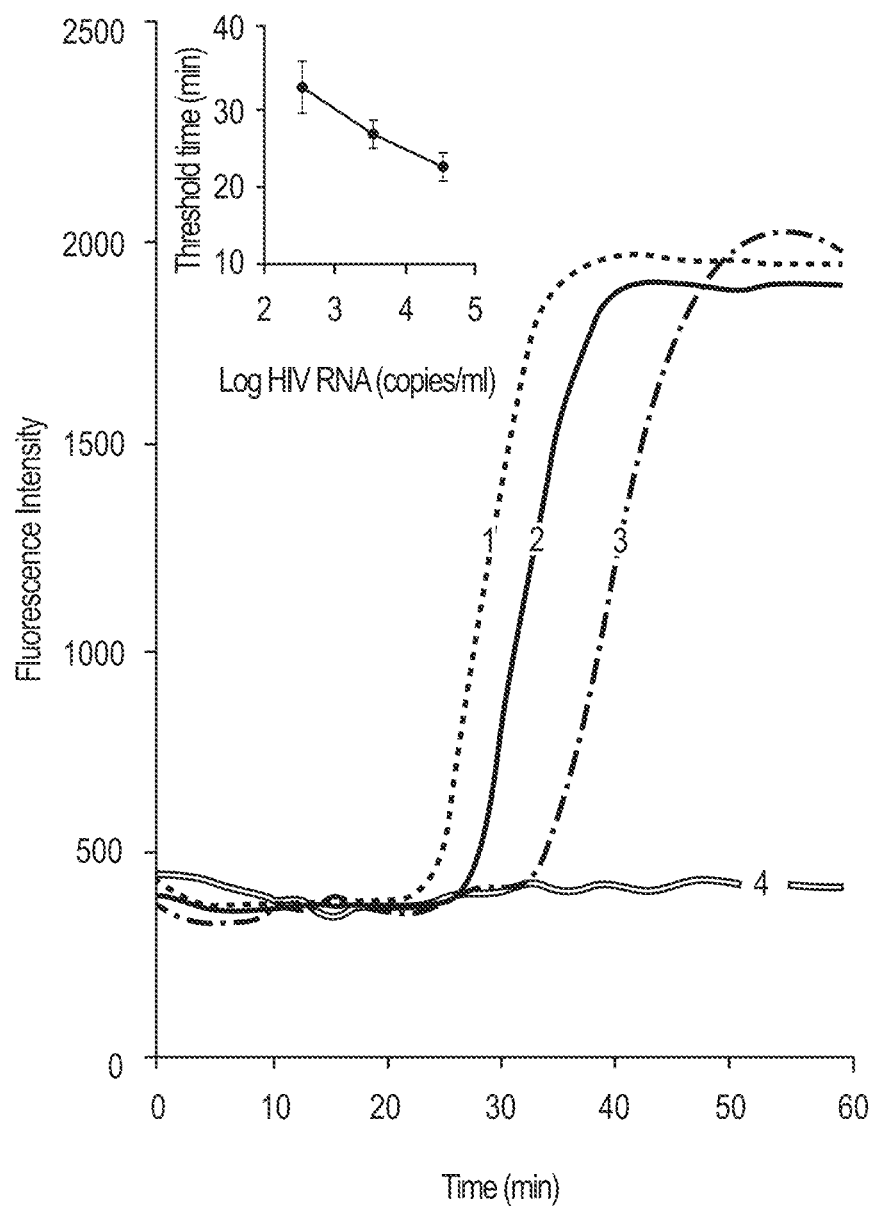

To test the suitability of the plasma extracted with the separator for POC, nucleic acid-based detection, the extracted plasma containing intact HIV virus at various concentrations may be tested on the microfluidic NAT chip shown in FIG. 6B. HIV-specific LAMP (loop mediated isothermal amplification) primers targeting regions of the HIV genome that are conserved among multiple subtypes may be used. The linearity range of the HIV assay may be determined as described in FIG. 6C. At least three replicates of each concentration is tested. Negative normal human blood samples may also be tested. Linear regression analysis may be used to correlate the linear relationship between the assay values and establish the standard curve for HIV-1 RNA quantitation.

A small randomized blinded study may be performed on clinical samples from de-identified individuals infected with HIV and with healthy controls. A total of 12 HIV-positive and 4 negative blood specimens may be tested. These samples may be split and repeatedly separated at least four times with separate, identical separators. To establish a reference, the same blood samples are centrifuged with a bench-top centrifugation. Both extracted plasma produced by the plasma separator and centrifuged plasma produced by benchtop centrifugation are analyzed by standard quantitative PCR to determine the viral titer. Results are analyzed and the data are decoded. All data analyses may be performed using log 10 transformed values. The correlation coefficient of the log copy number obtained in extracted plasma between the disclosed plasma separator and the benchtop centrifugation may be determined using SPSS version 10.0 (SPSS Inc., Chicago, Ill.).

Figure 7:
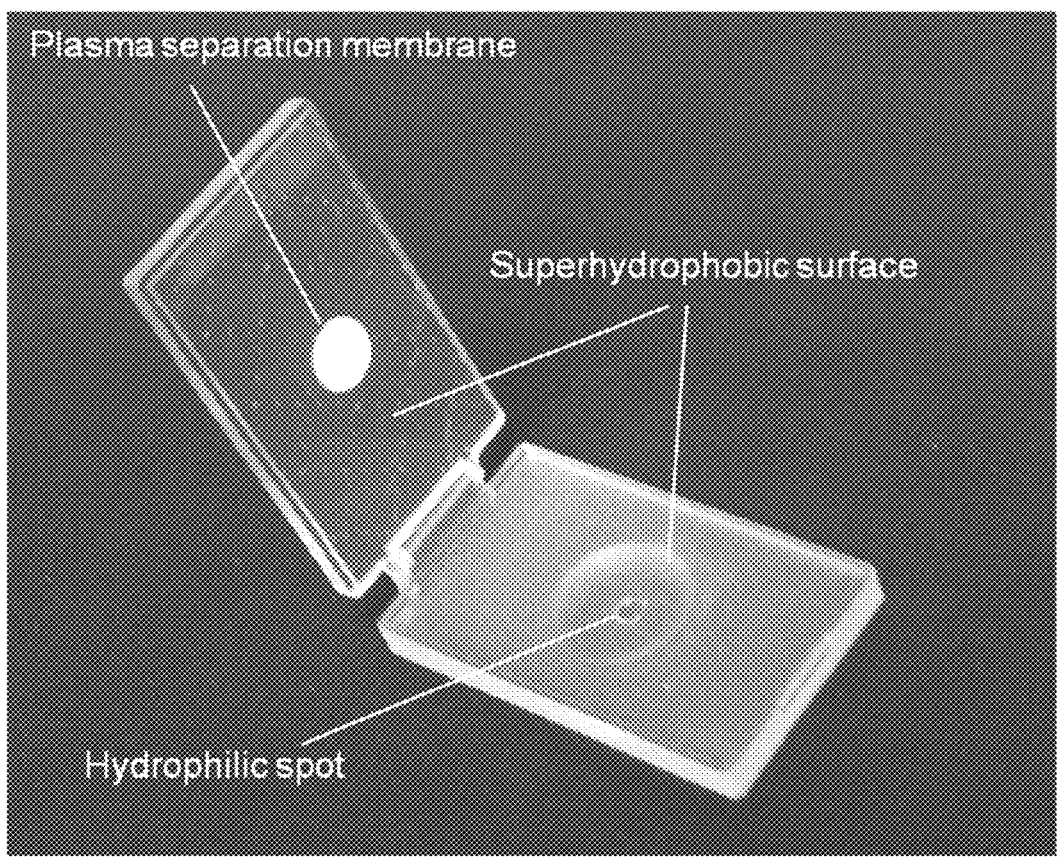
FIG. 7: Photograph of a 3D-printed exemplary superhydrophobic plasma separator. Again, it should be understood that devices described as being suitable for plasma separation are also suitable for serum separation as well.

FIG. 7 shows an exemplary embodiment of the disclosed devices. As shown in the figure, a device may include upper and lower superhydrophobic surfaces connected by a hinge. The hinge is illustrative only, as the two surfaces need not be physically connected. In some embodiments, the upper and lower surfaces are physically separate from one another and are engaged by the user (e.g., by clamping, clipping, screwing-down, and the like) at the time of use. The upper surface shown in the figure includes a plasma separation membrane that contacts a blood sample when the sample is placed in the well (not labeled) of the lower surface and the device is placed into an operating (e.g., closed) configuration. The well may include a hydrophilic spot (shown), which spot acts as a base or landing location for blood disposed into the well. In this way, blood is localized at the hydrophilic spot (by the action of the superhydrophobic surfaces) and is then contacted with the plasma separation membrane. Although not shown in the figure, the device may be oriented during operation such that gravity assists with the sedimentation of red blood cells when the blood is contacted to the separation membrane.

Hemolysis Detection

Figure 8:
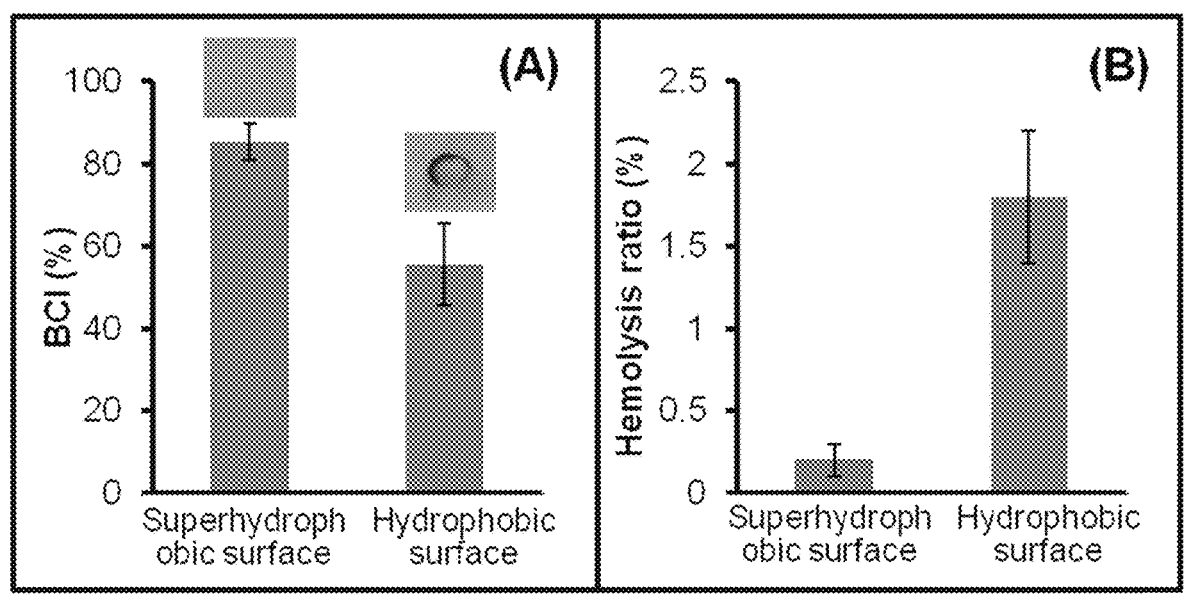
FIGS. 8A-8B: Illustrates blood clotting index (A) and hemolysis ratio (B) for blood processed by superhydrophobic surfaces and hydrophobic surfaces.
Figure 9:
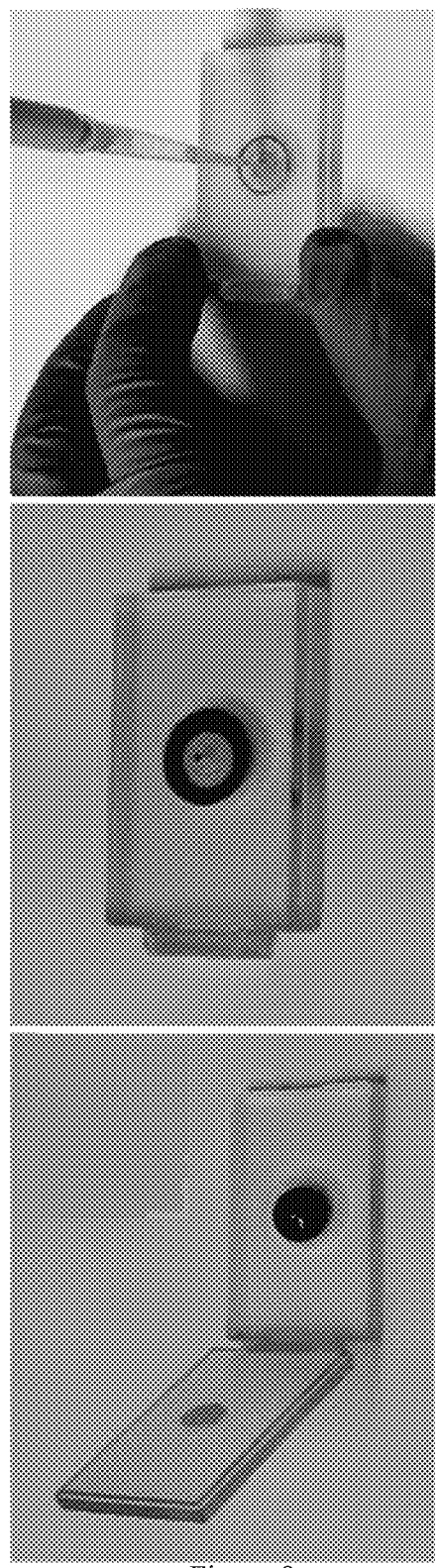
FIGS. 9A-9C: Illustrates operation of an exemplary embodiment of the disclosed technology, through the stages of (A) introduction of blood into device; (B) gravity-based sedimentation of red blood cells, and (C) collection of plasma.

With reference to FIG. 8, fresh blood (20 μL) was added to the samples for 20 min incubation and then 2 mL of normal saline was added to each sample to stop the hemolysis completely. Positive and negative controls were produced by adding 20 μL of blood to 2 mL of distilled water and normal saline, respectively. After incubation, the blood cells were removed by centrifugation. The hemolysis ratio was calculated based on the absorbance at 540 nm using a Nanodrop reader. The hemolysis ratio was calculated according to the following formula:

$$HR\ (\%) = (OD_{test} - OD_{neg})/(OD_{pos} - OD_{neg}) \times 100\%$$

Whole Blood Clotting Time

The anticoagulant properties of different superhydrophobic surface were evaluated by the clotting time method using fresh blood. Briefly, 20 μL of fresh blood were dropped onto the samples, followed by incubation at 37° C. for 20 min. Then 4 mL of deionized water were added to stop the reaction. The concentration of free haemoglobin in water was measured by a Nanodrop reader at 540 nm. The relative absorbency of 20 μL of whole blood diluted by 4 mL of distilled water was assumed to be 100. The blood clotting index (BCI) of a biomaterial can be quantified by the following equation:

$$BCI\ (\%) = (absorbency\ of\ sample\ solution)/(absorbency\ of\ fresh\ blood\ solution) \times 100$$

The surperhydrophobic surface shows a higher BCI compared with hydrophobic surface (A) since some blood was clotted and left on the hydrophobic surfaces (see inset in A).

Operation and Plasma Yield

With reference to FIG. 10, 300 μL volume of the whole blood spiked was manually loaded into the plasma separation (A). Then, the cover with a plasma separation membrane was closed and blood was sandwiched between two superhydrophobic substrates (B). The sandwiched blood was left to sediment for 5-10 min. During this time interval, blood cells settled toward the bottom. After cell sedimentation, the tip of a 200 μL Eppendorf pipet was inserted into the plasma exit port (C). A negative pressure was then applied with the pipet. The plasma filtered through the Vivid™ plasma separation membrane while the red blood cells (RBCs) and white blood cells (WBCs) were retained in the chamber. In this illustrative embodiment, the plasma yield was 73.6±15.5 μL of plasma, collected from 300 μl of whole blood.

Further Disclosure

To meet stringent limit-of-detection specifications for low abundance target molecules, a relatively large volume of plasma is usually needed in many blood-based clinical diagnostics. Although centrifugation is ubiquitously used in biomedical laboratories to separate plasma from whole blood, it is generally not accessible for on-site testing or bedside diagnostics. Here, is reported a simple, yet high-efficiency, clamshell-style, superhydrophobic plasma separator that is capable of separating a relatively large volume of plasma from several hundred microliters of whole blood (finger-prick blood volume).

A plasma separator may include a superhydrophobic top cover with a separation membrane and a superhydrophobic bottom substrate. The separation membrane in the disclosed devices may be positioned at the top of sandwiched whole blood film to increase the membrane separation capacity and plasma yield. In addition, the superhydrophobic characteristics of some embodiments of the disclosed technology (i) facilitate the formation of well-defined, contracted, thin blood film with a high contact angle; (ii) minimize biomolecular adhesion; (iii) increases blood clotting time; and (iv) reduces blood cell hemolysis. An exemplary device demonstrated a "blood in-plasma out" capability, consistently extracting 65±21.5 µL of plasma from 200 µL of whole blood in less than 10 min. The device was used to separate plasma from *Schistosoma mansoni* genomic DNA-spiked whole blood with a recovery efficiency of >84.5±25.8%. The *S. mansoni* genomic DNA in the separated plasma was successfully tested on a custom-made microfluidic chip by using loop mediated isothermal amplification (LAMP) method.

As explained elsewhere herein, plasma (or serum) extraction or separation from raw whole blood is usually required for blood-based clinical diagnostics because i) the inclusion of blood cells or components such as hemoglobin may inhibit subsequent DNA or RNA polymerases in enzymatic amplification tests (e.g., PCR), leading to an unreliable quantification or even false negatives; ii) inhibitors from whole blood can also interfere with immunoassays and result in low sensitivity; and iii) many accepted standards are based on pathogen levels in cell-free plasma rather than whole blood.

As one illustrative, non-limiting example, HIV viral load testing is based on detecting cell-free virus in blood, but not reverse-transcribed viral DNA integrated in the chromosomes of blood cells. In clinical laboratories, plasma separation is typically carried out with a bench-top centrifuge. However, centrifugation is not suitable for on-site or bedside applications. Centrifuges may also not be available in sufficient numbers even at hospitals in resource-constrained settings.

Recently, various approaches have been reported to extract plasma from whole blood at the point of care. including capillary imbibition, blood cell sedimentation, and cross-flow filtration. However, these methods either require a pre-dilution prior to blood separation or operate with minute volumes of blood (<10 µL). Extensive dilution may, however, adversely affect the limit-of-detection, which is critical in many clinical samples with relatively low abundance target molecules. Minute volumes of plasma cannot provide sufficient target for amplification such as needed for the monitoring of HIV viral load, and the detection of cell-free nucleic acids (cfNAs).

For example, the state of the art limit of detection of HIV viral load is 50 copies/mL. At this concentration, most 1 µL blood samples will contain no virus at all. Even if one is content with a limit of detection of 1000 copies/mL (a concentration of HIV virus that requires a change of therapy), many 1 µL blood samples will present negative.

Existing membrane configurations are susceptible to clogging, leading to a low separation capacity and low plasma yield. To address this shortcoming, some have tried a sedimentation-assisted plasma separator, but this device may be incompatible with onsite testing. In particular, children below 24 months of age are restricted to 700 µL of whole blood draws. In comparison, finger or heel-prick blood sampling is less invasive and more convenient than venipuncture sampling, and has been validated against standard phlebotomy in clinical testing.

There is a clear need for a high-efficiency, rapid, non-instrumented, point-of-care (POC) plasma separator for extracting a relative large volume of plasma from several hundred microliters of finger or heel-prick blood (maximum volume is 250-500 µL), instead of milliliters of venipuncture blood sampling.

Superhydrophobic surfaces, as seen in lotus leaves, typically have a water contact angle greater than 150° C. and a small roll-off angle (<10°). They are self-cleaning, that is, water droplets can roll off the surfaces at a very small tilt angle and carry away dust particles and debris. Superhydrophobic coatings have been applied to surfaces to repel bioparticles due to their excellent anti-adhesion and anti-biofouling properties. In recent years, there has been an increasing interest in incorporating superhydrophobic surfaces into microfluidic devices for fluid manipulation and bioanalytical application.

Here is disclosed, inter alia, a high-efficiency plasma separator for relatively large-volume plasma extraction from several hundred microliters of whole blood. The separator takes advantage of: i) the combination of gravitational sedimentation of blood cells and a top-positioned membrane filtration mechanisms to reduce membrane clogging and to enable the extraction of relatively large plasma volume, and ii) superhydrophobic characteristics, in some embodiments, to reduce the loss of target biomolecules and to prevent the sandwiched blood film from spreading. Demonstrated was an extraction of 65±21.5 µL of plasma from 200 µL of whole blood on the device within less than 10 minutes. The utility of this superhydrophobic plasma separator for molecular diagnostics application was demonstrated by separating plasma from *Schistosoma mansoni* DNA-spiked whole blood. The *S. mansoni* DNA in extracted plasma was tested in a microfluidic chip that carried out nucleic acid isolation and amplification, demonstrating that the plasma was of sufficient purity for polymerase activity. The plasma separator described herein can be used as a stand-alone module to separate the plasma from the whole blood.

Accordingly, the device is suitable for onsite testing at home, in the clinic, at bedside, as well as in resource-poor regions of the world, where funds, trained personnel, and laboratory facilities are in short supply, and in settings lacking electrical power.

Additional Disclosure

Superhydrophobic Plasma Separator

An exemplary clamshell-style, superhydrophobic plasma separator was 5.4 cm long×3.0 cm wide×0.8 cm thick, as shown in FIG. 11. Both top and bottom substrates were fabricated by 3D printing (Projet 6000HD, 3D Systems, USA), and hinged together by a pivot joint. The bottom substrate contains a 13 mm diameter×1.3 mm depth blood well for holding 200 µL of blood; the top cover has 11-mm diameter×0.5 mm deep depression to hold a plasma separation membrane (Vivid™, Pall Life Sciences, East Hills, N.Y.). An array of micropillars, 300 µm tall and 500-µm in diameter each, was printed into the floor of the depression (inset in FIG. 11B). The micropillar array serves as a support for the plasma separation membrane. The micropillar array cavity connects to a 1.5 mm diameter vertical vias (plasma exit port) (inset in FIG. 11B). The size of the exit port was designed to match tightly the outer diameter of a 200 µL pipette tip that was used to collect the plasma. To form a thin superhydrophobic coating on both substrates, a commercially available, spray-on "Neverwet™" was applied in a two-step process suggested by the manufacturer.[42]

An 11 mm diameter, separation membrane was cut by a $CO_2$ laser cutter (Universal Laser Systems). A double-sided adhesive tape (McMaster-Carr, New Brunswick, N.J.) was cut with the laser to the same external dimensions as the membrane. An 8 mm diameter circle (an area of ~0.5 cm²) was removed from the adhesive tape center to leave an annular frame. The adhesive frame was attached to the plasma separation membrane. The resulting laminate was placed on the top of the micropillar array and pasted to the frame surrounding the micropillar array to entirely cover the micropillar array.

Blood Compatibility Characterization of Spray-On Superhydrophobic Surface

The morphologies of the spray-on superhydrophobic surface were imaged by scanning electron microscope (SEM) equipped with a focused ion-beam (FIB) (FEI Strata DB235). To determine whether such superhydrophobic surfaces can reduce biomolecular adhesion, sandwiched 100 µL of plasma sample spiked with a known S. mansoni DNA concentration (50 fg) was sandwiched between the two spray-on superhydrophobic substrates.

After 10 min, the plasma was recovered, and the S. mansoni DNA in the plasma was detected by real time quantitative loop-mediated isothermal amplification (LAMP). To test the anticoagulant property of the spray-on superhydrophobic coating, 30 µL of fresh blood was dropped onto the surface, followed by incubation at 37° C. for 20 min. Then, the blood was rinsed by DI water. To assess the hemocompatibility of the coating, 200 µL of whole blood sample was placed on the coated substrate. After 20 min, 4 mL of isotonic saline was added to the blood sample to stop hemolysis. Positive and negative controls were produced by adding 200 µL of whole blood to 4 mL of distilled water and isotonic saline, respectively. All the test samples were centrifuged. Optical density (OD) of the supernatant was measured at 540 nm using a ND-1000 spectrophotometer (NanoDrop Technologies, Wilmington, Del.).

Sample Preparation and Device Testing

De-identified, EDTA anticoagulated, whole blood samples from healthy donors were collected by the Hospital of the University of Pennsylvania with the approval of the Institutional Review Board (protocol: 814752). All blood samples were handled without any dilution.

200 µL of the whole blood spiked with S. mansoni DNA (obtained from the Schistosomiasis Resource Center, for distribution by BEI Resources, NIAID, NIH) was loaded into the blood well (FIG. 12A). Then, the plasma separator was closed and the whole blood was sandwiched between two superhydrophobic substrates and formed a thin, blood film (FIG. 12B). The sandwiched blood film was left to sediment for 7-10 min. As seen in the inset of FIG. 12B, the blood cells settled towards the bottom of the blood film. After cell sedimentation at room temperature (20-25° C.), the tip of a 200 µL Eppendorf pipette (Brinkman Instruments, Inc., Westbury, N.Y.) was inserted into the plasma exit port to collect plasma (FIG. 12C). The plasma containing S. mansoni DNA filtered through the Vivid™ plasma separation membrane, while the red blood cells (RBCs) and white blood cells (WBCs) were retained in the blood well.

The separator's recovery efficiency for S. mansoni DNA was evaluated against standard laboratory procedures. To establish a reference, anti-coagulated whole blood samples containing S. mansoni DNA at various concentrations were centrifuged at a full speed (14,000 rpm) for 10 min using a bench-top centrifuge at room temperature (Labnet International Inc., Woodbridge, N.J.). Both S. mansoni DNA-laden plasma samples extracted with the plasma separator and separated by the bench-top centrifuge were analyzed by real time LAMP. The S. mansoni DNA amount in the plasma samples separated with the disclosed devices and that of the centrifuged plasma were then compared.

S. mansoni Genomic DNA Testing

The S. mansoni DNA in the separated plasma was subsequently extracted and amplified in a custom-made microfluidic chip that contained three independent, multifunctional, isothermal amplification reactors (MIAR). Each of these reactors was equipped with a flow-through Qiagen™ silica membrane (QIAamp DNA Blood Mini Kit) at its entry port. The 30 µL of plasma collected with the plasma separator was mixed with 30 µL of Qiagen™ lysis buffer and inserted into one of the amplification reactors. The nucleic acids bound to the Qiagen™ silica membrane. Subsequent to the sample introduction, 50 µL of Qiagen™ wash buffer 1 (AW1) was injected into the chip to remove any remaining amplification inhibitors. Then, the silica membrane was washed with 50 µL of Qiagen™ wash buffer 2 (AW2), followed by air-drying for 30 seconds. Next, 22 µL of LAMP master mixture, which contained all the reagents necessary for the LAMP including 0.5×EvaGreen® fluorescence dye (Biotium, Hayward, Calif.), was injected into each reaction chamber through the inlet port.

The target for LAMP amplification was the highly-repetitive Sm1-7 sequence found in S. mansoni genomic DNA. Primers were as described.[44] The molecular diagnostic chip was placed on a homemade, portable heater and heated to 63° C. for ~60 minutes. The fluorescence excitation and emission imaging were carried out with a handheld, USB-based, fluorescence microscope (AM4113T-GFBW Dino-Lite Premier, AnMo Electronics, Taipei, Taiwan).[45]

Results and Discussions

Biocompatibility of the Spray-on Superhydrophobic Surface

Figure 13A:
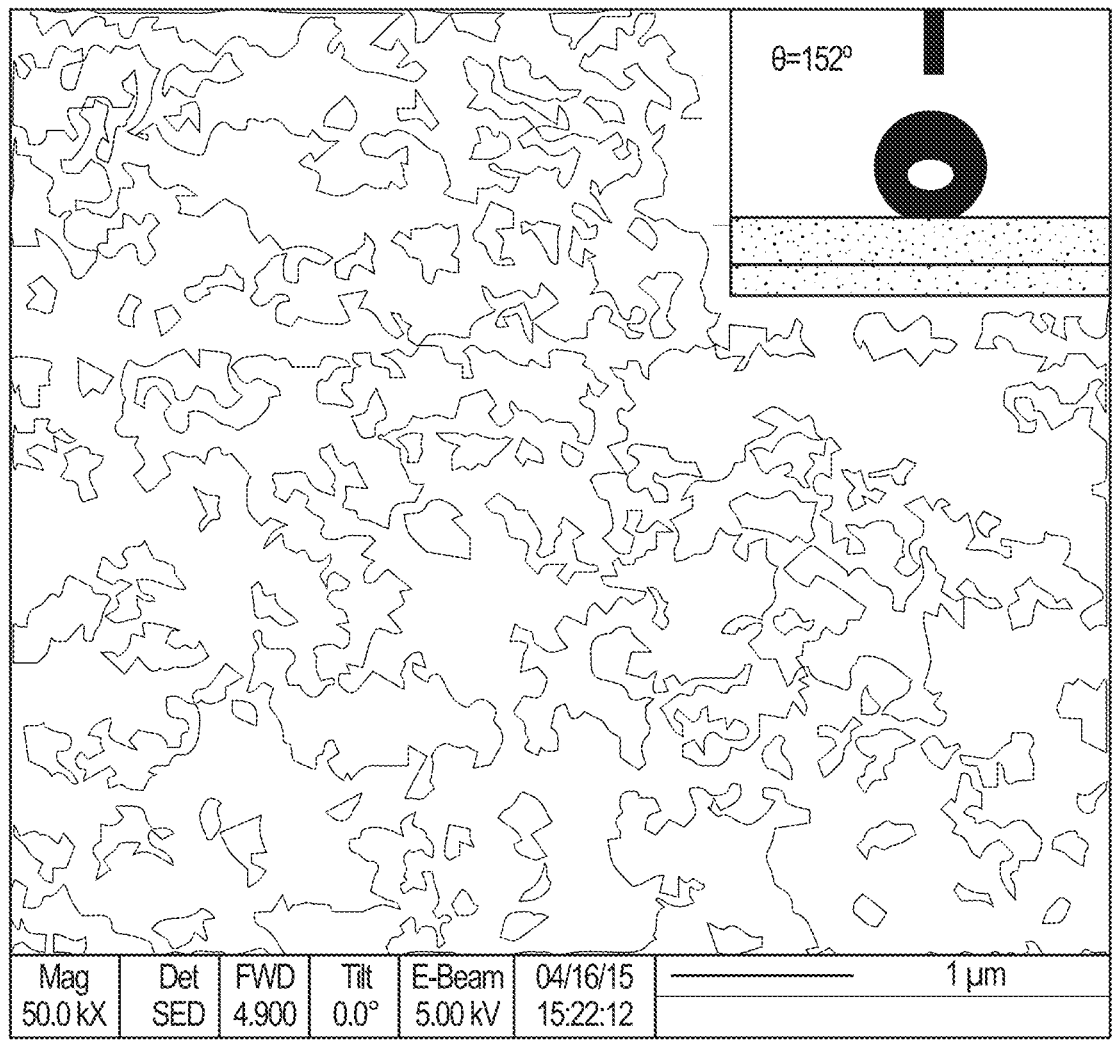
FIGS. 13A-13B provides SEM images of the substrates with (A) and without (B) the spray-on superhydrophobic coating. Inset: static water contact angle of a 5-µL water droplet on the respective surface.
Figure 13B:
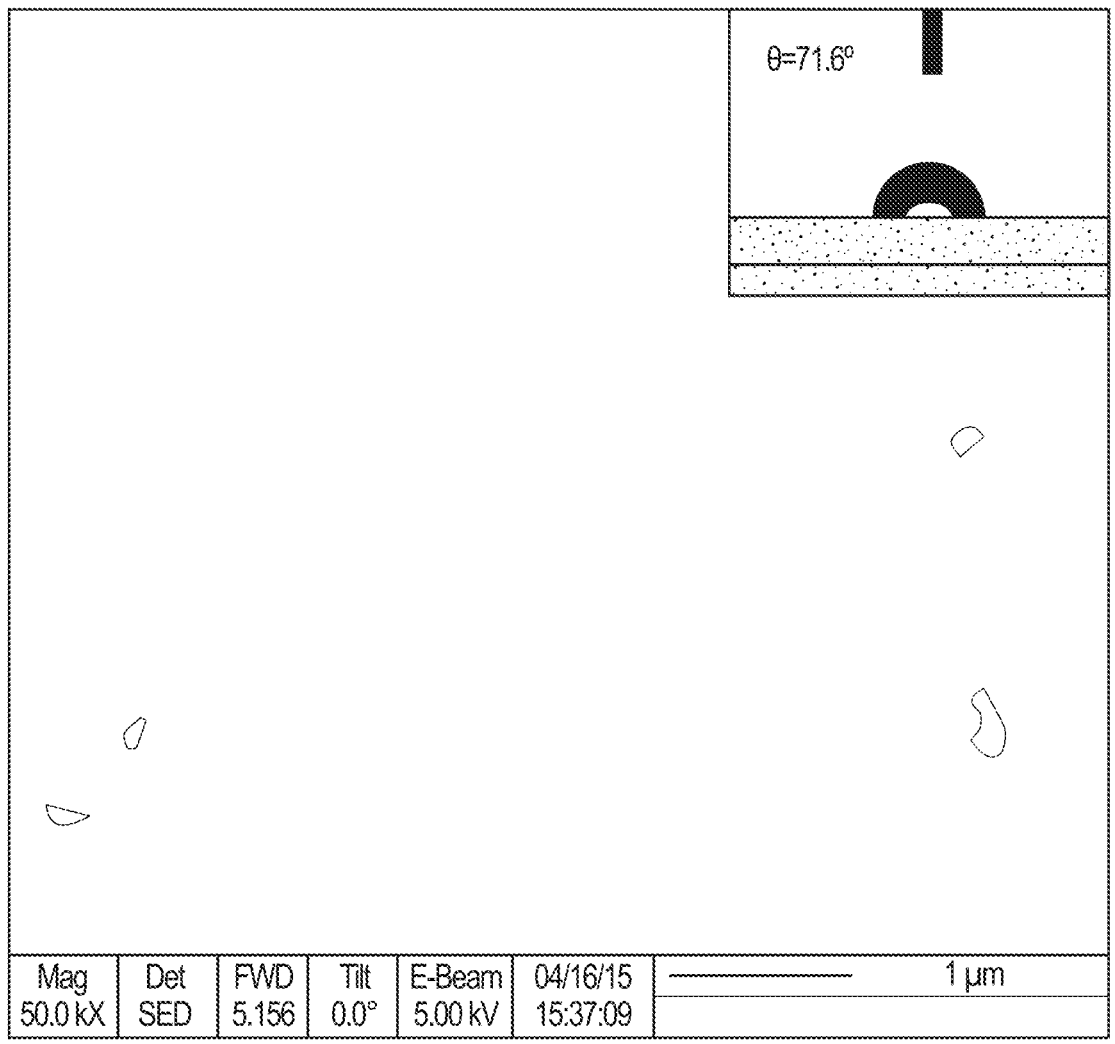

Inspired by nature, various methods for the preparation of biomimetic superhydrophobic surfaces have been reported, including electrochemical deposition, templating method, self-assembly, and micro-/nanofabrication. Here, a superhydrophobic coating was sprayed on the separator by using a commercially available "Neverwet™" because of its simplicity, low cost, and compatibility with various materials. FIG. 13 shows the surface morphology of the spray-on superhydrophobic coating substrate and non-coated 3D printed substrate. There is micro-/nano-scale surface roughness on the "Neverwet™" coating surface (FIG. 13A), rendering the surface superhydrophobic with a water contact angle of 152° (inset in FIG. 13A). In contrast, the uncoated substrate shows a smooth surface (FIG. 13B) with a contact angle of 71.6° (inset in FIG. 13B).

Also evaluated was the biocompatibility of the spray-on superhydrophobic coating, with regard to biomolecular adhesion, blood-clotting time, and hemocompatibility. The spray-on superhydrophobic coating had only 2.6% DNA loss, which was 9 times lower than that of the non-coated substrate (23.9%) for 0.5 pg/mL S. mansoni genomic DNA in plasma. Without being bound to any particular theory, this reduction in absorption may be attributed to the reduced liquid-solid contact area due to the presence of air pockets entrapped between the micro-/nanoscale hierarchical structures of the superhydrophobic coating. Hemolysis should be avoided since lysis of red blood cells introduces hemoglobin, a strong inhibitor of both enzymatic amplification and ELISA, into the plasma. In the presence of hemoglobin, there are two absorbance peaks at 540 and 576 nm.

Figure 16A:
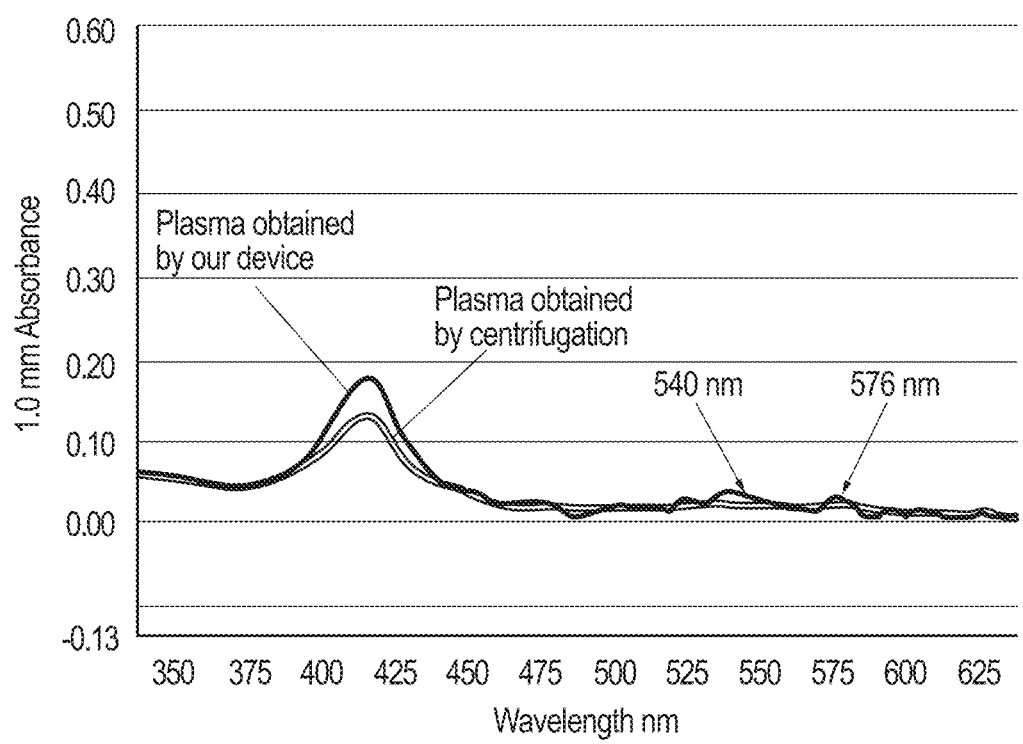
FIGS. 16A-16B provide (A) Absorbance spectrum of plasma extracted by a superhydrophobic plasma separator (black) and by benchtop centrifugation (red). (B) Optical images of plasma isolated with the device and centrifuged plasma.
Figure 16B:
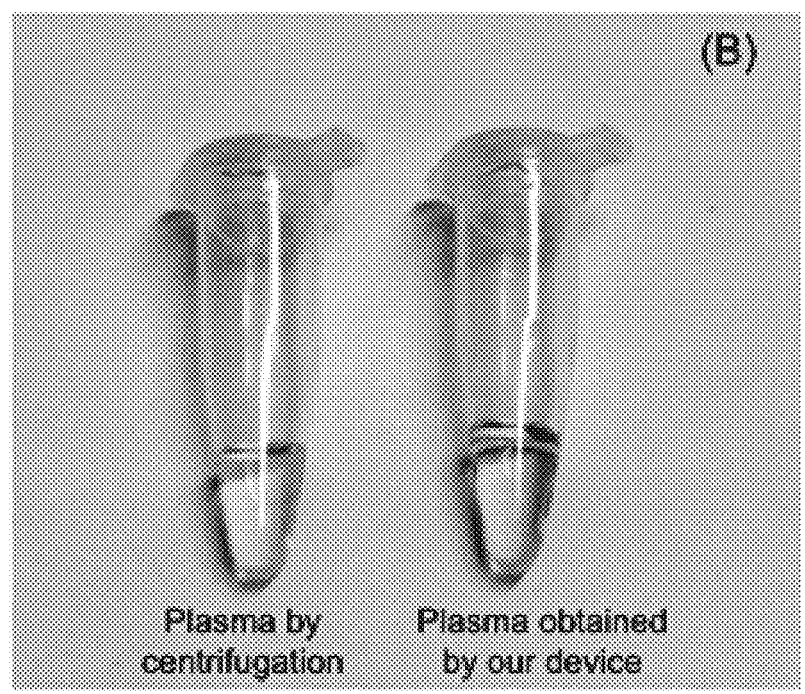

Compared also were the absorbance spectra of the plasma extracted by the device to the centrifuged plasma using a benchtop instrument (FIG. 16). There is no obvious absorbance peak for the on-chip separated plasma sample, comparable with that of the benchtop centrifugation method. In addition, clotting was not observed on the superhydrophobic surface (FIG. 14A) after incubation with 30 µL of whole blood at 37° C. for 20 min. In contrast, a large blood clot appeared on the surface of the uncoated substrate (FIG. 14B), suggesting that the superhydrophobic surface had good blood compatibility in preventing thrombus formation. To assess the hemocompatibility of the superhydrophobic coating, the hemolysis rate (HR) was defined as the ratio of the optical density (OD) difference between the test sample ($OD_{test}$) and the negative control ($OD_{negative}$) vs. the OD difference of the positive ($OD_{positive}$) and negative ($OD_{negative}$) controls. Experiments showed that the hemolysis ratio of blood on the spray-on superhydrophobic surface was about one-ninth of that of the uncoated substrate, providing direct evidence of the enhanced hemocompatibility of the superhydrophobic surface.

The top-positioned membrane configuration allows for gravitational sedimentation of the blood cells in an opposite direction to the membrane surface (Inset in FIG. 12B) rather than precipitation directly onto the membrane. This arrangement reduces the membrane blockage by blood cells and increases the membrane separation capacity without excessive hemolysis. A superhydrophobic plasma separator with a top-positioned separation membrane was capable of extracting 65±21.5 µL (n=10) of plasma from 200 µL of undiluted whole blood, corresponding to a separation capacity of 130 µL/cm², which is 6.5 times higher than the theoretical value (20 µL/cm²) of the Vivid™ membrane.

Figure 12:
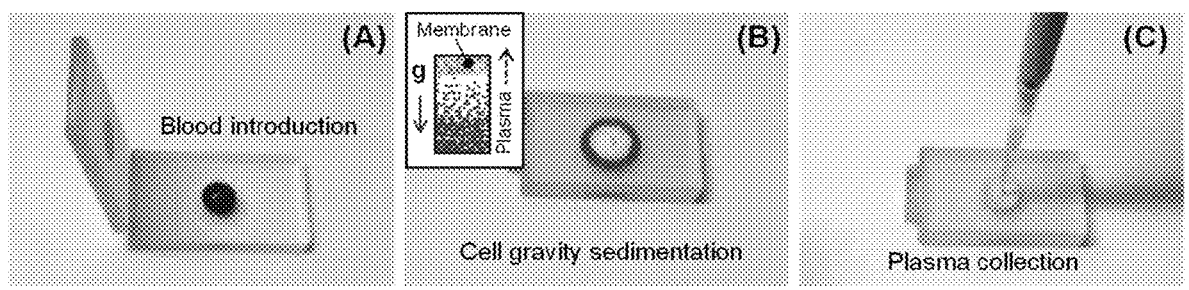
FIGS. 12A-12C A sequence of images illustrating the plasma separation process. (A) A 200 µL of blood sample spiked with S. mansoni DNA was loaded into the superhydrophobic plasma separator. (B) When the top cover was closed, the blood was sandwiched between the two superhydrophobic substrates and formed a thin blood film. (C) Plasma collection.
Figure 14:
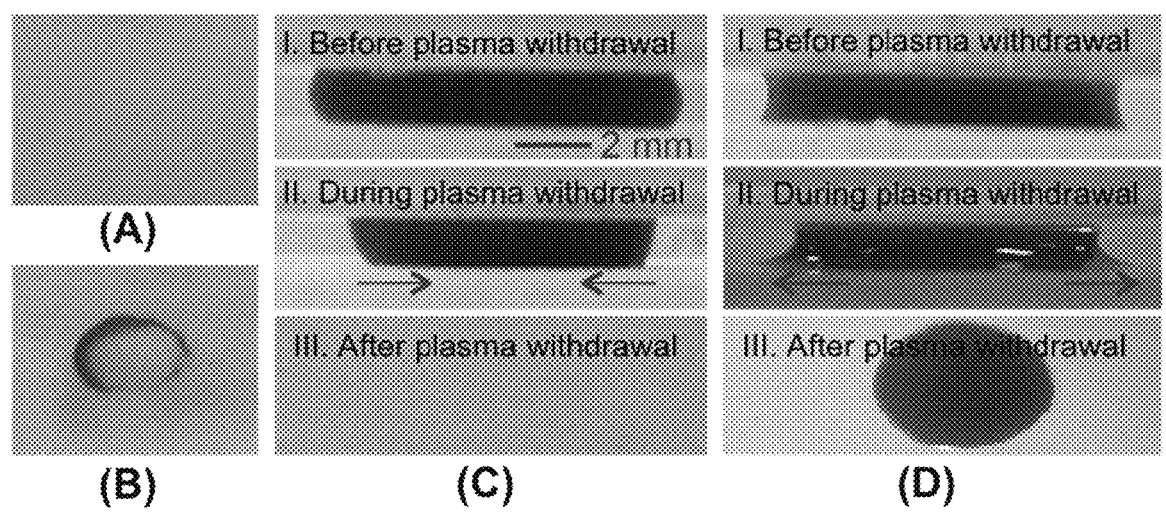
FIGS. 14A-14D provide photographs of blood clots on the spray-on superhydrophobic coating substrate (A) and the uncoated substrate (B) after incubation with whole blood at 37° C. for 20 min. A sequence of images illustrating the plasma separation from the sandwiched whole blood film between two superhydrophobic coating substrates (C) and uncoated substrates (D).

FIGS. 12 and 14C illustrate the operation of the superhydrophobic plasma separator. When blood was sandwiched between two superhydrophobic substrates, a thin, well-defined, blood film with a high contact angle was formed as shown in FIG. 14C-I. When plasma was withdrawn, the sandwiched blood film contracted (indicated by arrows in FIG. 14C-II) and no blood was left on the superhydrophobic coating substrate (FIG. 14C-III) after plasma withdrawal, in sharp contrast with the performance of the uncoated substrates, in which case the blood spread and remained (FIG. 14D).

Because the blood cells are denser than the plasma, they would sink to the bottom of the thin blood film, leading to the formation of a cell concentration gradient. After sedimentation, a pipette was inserted into the plasma exit port at the top cover (FIG. 12C).

When a negative pressure was applied to the pipette, the resulting pressure difference across the membrane induced plasma flow through the membrane while the blood cells were left behind. Most of the plasma that flowed through the membrane came from the top layer of the thin blood film, where the blood cells were least concentrated, allowing the membrane to purify a much greater volume of plasma than that in a horizontal position. Although the illustrative device was designed to extract plasma from 200 µL of whole blood (maximum volume of finger-prick blood sampling is 250-500 µL), the device can be tailored for other volumes of whole blood.

S. mansoni Genomic DNA Detection on a Molecular Diagnostic Chip

Figure 17:
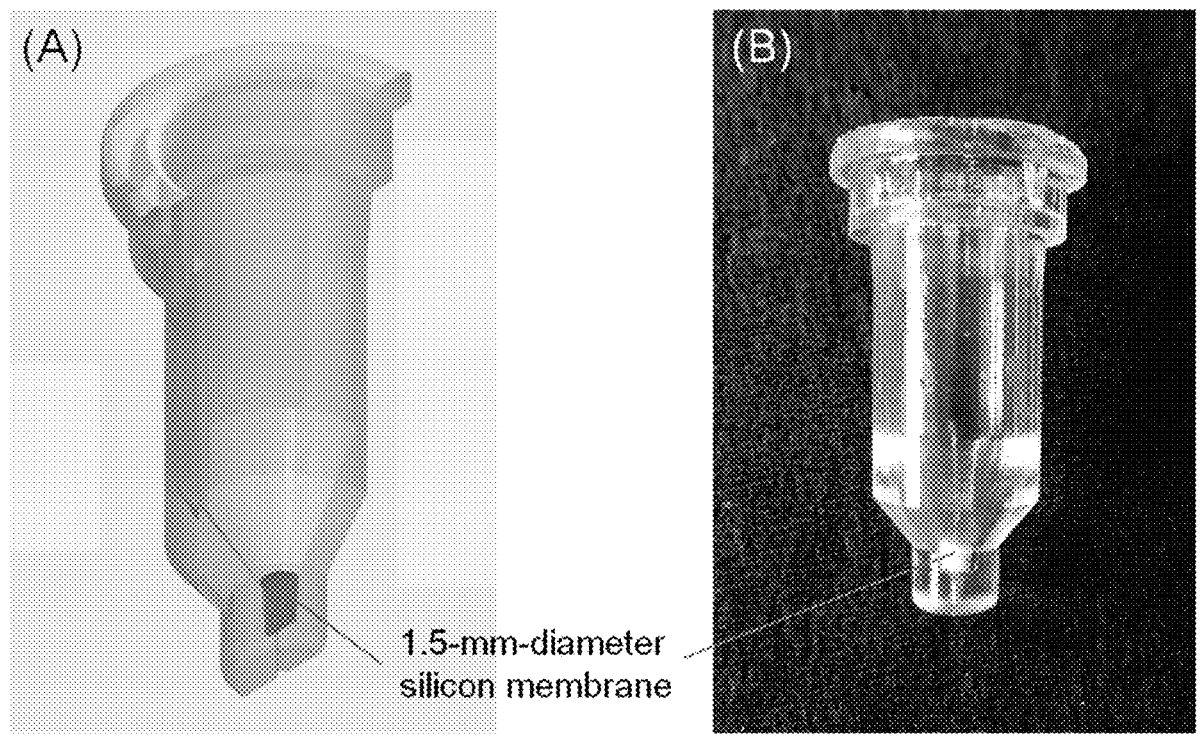
FIGS. 17A-17B illustrate a 3D printed tube with 1.5-mm-diameter silicon membrane for cell-free schistosome genomic DNA extraction: (A) schematic illustration of 3D printed tube and (B) a photograph of the 3D printed tube.

Schistosomiasis is the second most prevalent parasitic disease in the tropics and subtropics. About 779 million people in 77 endemic countries live in areas where the risk of infection is high. Because one objective in separating the plasma from the whole blood is to detect cell-free DNA and plasma pathogens by molecular diagnostics, it is necessary to know whether the separation process affects the S. mansoni genomic DNA concentration in plasma. Loss of targets can occur, for example, due to non-specific binding of the DNA to the separation membrane and the structural constituents of the separator, e.g. the micropillar array with a relatively high surface area. To test the DNA recovery, a homemade, 3D printed tube (FIG. 17) with a 1.5-mm diameter Qiagen™ silica membrane was adapted to extract S. mansoni genomic DNA from 30 µL of the separated plasma. The extracted DNA was quantified by real time LAMP method on a benchtop PCR machine. The on-chip extracted plasma showed a S. mansoni genomic DNA recovery yield of >84.5±25.8% (n=3) (FIG. 15A) when compared with the traditional centrifugation method. As the S. mansoni genomic DNA in the whole blood increased, so did the recovery which could be due to the saturation of surface binding sites in the device. These results clearly demonstrate that a superhydrophobic plasma separation device with a top-positioned membrane configuration is applicable to clinical testing with downstream detection assays with minimal loss of target biomolecules.

Figure 15:
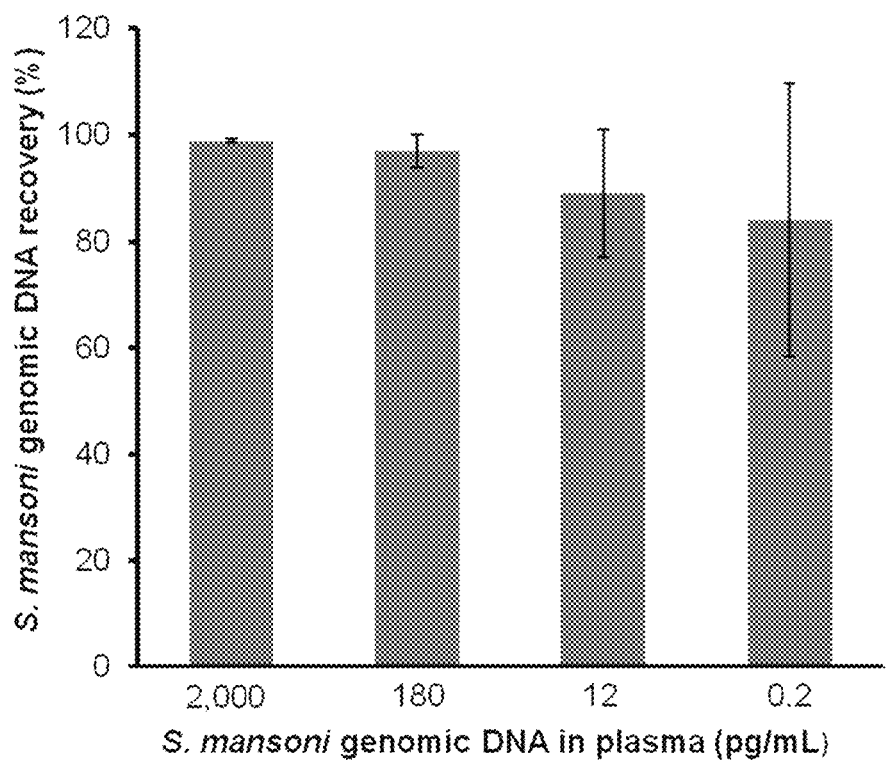
FIGS. 15A-15B provide (A) Recovery efficiency of S. mansoni genomic DNA on the exemplary plasma separator at various concentrations. (B) Endpoint, fluorescence images of intercalating dye in three amplification chambers, DNA amount in each chamber is 10 fg, 1 fg and 0 fg (negative control) (left to right). The dash squares indicate the location of the amplification reactors.
Figure 15:
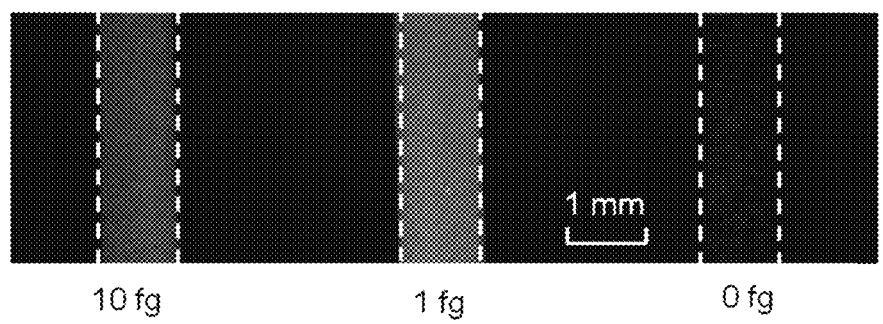

To test the suitability of the plasma extracted with the separator for point-of-care, nucleic acid-based detection, plasma was separated from schistosome DNA-spiked blood using the device, and then carried out the amplification process in the molecular diagnostic chip. FIG. 15B showed fluorescence images of intercalating fluorescent dye in three amplification chambers of the molecular diagnostic chip at the end of LAMP amplification of plasma samples spiked with different concentration of S. mansoni genomic DNA. The target S. mansoni genomic DNA amount in each chamber was 10 fg, 1 fg and 0 fg (left to right).

The test reaction chambers with positive samples emitted a strong green fluorescence due to the amplification of target DNA molecules while the negative control chamber did not. The molecular diagnostic chip was able to detect as little as 0.5 fg of S. mansoni genomic DNA (based on the S. mansoni genome size of ~365 Mb[56], a single genome equivalent is 0.4 pg). This experiment indicated that the plasma separated by the superhydrophobic plasma separator was suitable for nucleic acid amplification.

Exemplary Serum Separation

800 µL of fresh whole blood was loaded into the blood well of a plasma/serum separator (FIG. 1). Then, the separator was closed and the whole blood was sandwiched between two superhydrophobic substrates and formed a thin, blood film. The sandwiched blood film was left to sediment for 5 min.

Figure 18:
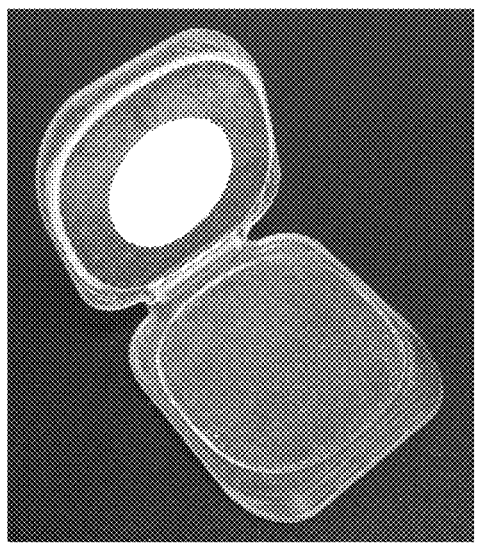
FIG. 18 illustrates an exemplary plasma/serum separator after the serum was removed.

After cell sedimentation and coagulation at room temperature (20-25° C.), the tip of a 200 µL Eppendorf pipette (Brinkman Instruments, Inc., Westbury, N.Y.) was inserted into the plasma/serum exit port to collect serum. The separator separated 100±20 µL of serum from 800 µL of whole blood. FIG. 18 is a photograph of the plasma/serum separator after the serum was removed.

Summary

As an example of the disclosed technology, a high-efficiency, clamshell-style, superhydrophobic plasma separator was used for extraction of 65±21.5 µL of plasma from 200 µL of whole blood by incorporating de-wetting phenomena attributed to superhydrophobicity on the surfaces of the separator. Unique to the device is the combined use of multiple separation principles and strategies, including cell sedimentation, size-based filtration, and a so-called lotus-leaf effect. A top-positioned, membrane-based, separation mechanism showed positive performance with respect to sample volume capacity and plasma yield, while the superhydrophobic surfaces offer minimal hemolysis or contamination of the plasma with substances such as hemoglobin, and reduce losses of the target analytes (i.e. DNA) due to unwanted surface binding. Further, the device may be made using a 3D printer, making it amenable to customization and continued optimization. Most importantly, the working principle and implementation are scalable, e.g., to blood sample volumes in excess of 1 mL, if desired.

Demonstrated here is that plasma extracted with the disclosed separators is appropriate for molecular detection of target analytes contained in whole blood by spiking blood with *S. mansoni* genomic DNA and using the plasma in the microfluidic-based nucleic acid amplification. Also demonstrated was a high efficiency recovery (>84.5±25.8%). The superhydrophobic, easy-to-use plasma separator reported herein can be used as a stand-alone separation device at home, in the clinic, as well as in resource-constrained settings where funds and trained personnel are in short supply. Moreover, the simplicity of the format, non-instrumented operation and the ability to integrate with existing microfluidic devices allows for convenient uses in downstream processing and analysis.

What is claimed:

1. A device for biological fluid separation, comprising:
    an upper surface and a lower surface, the device being configured such that in an open state, the lower surface is in fluid communication with the environment exterior to the device, and the device being configured such that in a closed state, the upper and lower surfaces are positioned opposite one another so as to define a volume between the surfaces; and
    at least one separation membrane being disposed in the upper surface, the separation membrane being positioned so as to be in fluid communication with the volume between the surfaces when the device is in the closed state, and the separation membrane being selectively permeable to a fluid blood component,
    wherein the lower surface comprises a hydrophilic region at least partially in register with the membrane when the device is in the closed state.

2. The device of 1, wherein the upper surface further comprises a hydrophobic region, a superhydrophobic region, or both.

3. The device of claim 1, wherein the lower surface further comprises a hydrophobic region, a superhydrophobic region, or both.

4. The device of claim 1, further comprising a fluid collection channel configured to be in fluid communication with the separation membrane when the device is in the closed state.

5. The device of claim 1, wherein the volume between the surfaces is further defined by a spacer.

6. The device of claim 1, wherein the device further comprises one or more reagents disposed within the volume between the surfaces.

7. The device of claim 6, wherein the one or more reagents comprises lyophilized heparin, lyophilized thrombin, citrate, a coagulant, EDTA, or any combination thereof.

8. The device of claim 6, wherein the one or more reagents are disposed on a hydrophobic region of the device, on a superhydrophobic region of the device, or both.

9. The device of claim 1, wherein the fluid blood component is blood plasma.

10. The device of claim 1, wherein the fluid blood component is blood serum.

11. The device of claim 1, the device further comprising one or more projections configured to support the separation membrane.

12. The device of claim 11, wherein one or more of the projections comprises a micropillar, a microcone or a microhexahedron.

13. The device of claim 1, wherein the upper and lower surfaces are positioned opposite one another such that a distance between the surfaces is between about 1 µm and about 1 cm.

14. The device of claim 1, wherein the volume between the surfaces is between about 1 µL and 5,000 µL.

15. The device of claim 1, wherein the upper and lower surfaces are connected by a hinge.

16. The device of claim 1, the hydrophilic region is a spot surrounded by a hydrophobic region.

17. A device for biological fluid separation, comprising:
    an upper surface and a lower surface each comprising a superhydrophobic region, the device being configured such that in an open state, the lower surface is in fluid communication with the environment exterior to the device, and the device being configured such that in a closed state, the upper and lower surfaces are positioned opposite one another so as to define a volume between the surfaces; and
    at least one separation membrane being disposed in the upper surface, the separation membrane being positioned so as to be in fluid communication with the volume between the surfaces when the device is in the closed state, and the separation membrane being selectively permeable to blood plasma.

18. The device of claim 17, further comprising a fluid collection channel configured to be in fluid communication with the separation membrane when the device is in the closed state.

19. The device of claim 17, wherein the device further comprises one or more reagents disposed within the volume between the surfaces.

20. The device of claim 17, wherein the lower surface comprises a hydrophilic region at least partially in register with the membrane when the device is in the closed state.

* * * * *

UNITED STATES PATENT AND TRADEMARK OFFICE
CERTIFICATE OF CORRECTION

PATENT NO. : 10,690,653 B2
APPLICATION NO. : 15/534810
DATED : June 23, 2020
INVENTOR(S) : Liu et al.

Page 1 of 1

It is certified that error appears in the above-identified patent and that said Letters Patent is hereby corrected as shown below:

In the Specification

Column 10, Line 5, Replace:
"methods are all suitable for positioning. The the separation"
With:
--methods are all suitable for positioning. The separation--

Column 15, Line 21, Replace:
"of each concentration is tested. Negative normal human"
With:
--of each concentration are tested. Negative normal human--

In the Claims

Claim 2, Column 23, Replace:
"The device of 1, wherein the upper surface further"
With:
--The device of claim 1, wherein the upper surface further--

Signed and Sealed this
Tenth Day of November, 2020

Andrei Iancu
*Director of the United States Patent and Trademark Office*